US011085008B2

(12) United States Patent
Dihora et al.

(10) Patent No.: US 11,085,008 B2
(45) Date of Patent: Aug. 10, 2021

(54) METHODS FOR MAKING COMPOSITIONS CONTAINING MULTIPLE POPULATIONS OF MICROCAPSULES

(71) Applicant: The Procter & Gamble Company, Cincinnati, OH (US)

(72) Inventors: Jiten Odhavji Dihora, Liberty Township, OH (US); Marc Adam Flickinger, West Chester, OH (US); Jianjun Justin Li, West Chester, OH (US); Johan Smets, Lubbeek (BE)

(73) Assignee: The Procter & Gamble Company, Cincinnati, OH (US)

( * ) Notice: Subject to any disclaimer, the term of this patent is extended or adjusted under 35 U.S.C. 154(b) by 496 days.

(21) Appl. No.: 15/198,248

(22) Filed: Jun. 30, 2016

(65) Prior Publication Data

US 2017/0002302 A1    Jan. 5, 2017

Related U.S. Application Data

(60) Provisional application No. 62/186,575, filed on Jun. 30, 2015.

(51) Int. Cl.
| | | |
|---|---|---|
| *C11D 3/50* | (2006.01) | |
| *B01J 13/04* | (2006.01) | |
| *C11B 9/00* | (2006.01) | |
| *C11D 17/00* | (2006.01) | |
| *A61K 8/11* | (2006.01) | |
| *A61K 8/37* | (2006.01) | |
| *A61Q 5/02* | (2006.01) | |
| *A61Q 5/12* | (2006.01) | |
| *A61Q 13/00* | (2006.01) | |
| *A61Q 15/00* | (2006.01) | |
| *A61Q 19/00* | (2006.01) | |
| *C11D 11/00* | (2006.01) | |

(52) U.S. Cl.
CPC ............... *C11D 3/505* (2013.01); *A61K 8/11* (2013.01); *A61K 8/37* (2013.01); *A61Q 5/02* (2013.01); *A61Q 5/12* (2013.01); *A61Q 13/00* (2013.01); *B01J 13/043* (2013.01); *C11B 9/0015* (2013.01); *C11B 9/0019* (2013.01); *C11B 9/0034* (2013.01); *C11B 9/0061* (2013.01); *C11B 9/0076* (2013.01); *A61K 2800/412* (2013.01); *A61K 2800/56* (2013.01); *A61K 2800/592* (2013.01); *A61Q 15/00* (2013.01); *A61Q 19/00* (2013.01); *C11D 11/0017* (2013.01); *C11D 17/0039* (2013.01)

(58) Field of Classification Search
None
See application file for complete search history.

(56) References Cited

U.S. PATENT DOCUMENTS

| | | | |
|---|---|---|---|
| 4,234,627 A | 11/1980 | Schilling | |
| 4,514,461 A | 4/1985 | Woo | |
| RE32,713 E | 7/1988 | Woo | |
| 4,882,220 A | 11/1989 | Ono et al. | |
| 4,898,680 A * | 2/1990 | Clauss | C11D 3/001 510/101 |
| 4,917,920 A | 4/1990 | Ono et al. | |
| 5,508,259 A | 4/1996 | Holzner et al. | |
| 6,200,949 B1 | 3/2001 | Reijmer et al. | |
| 6,645,479 B1 | 11/2003 | Shefer et al. | |
| 6,653,277 B1 | 11/2003 | Golz-Berner et al. | |
| 9,186,642 B2 | 11/2015 | Dihora | |
| 2003/0158344 A1 | 8/2003 | Rodrigues et al. | |
| 2003/0165692 A1 | 9/2003 | Koch et al. | |
| 2003/0195133 A1 | 10/2003 | Shefer et al. | |
| 2003/0203829 A1 | 10/2003 | Shefer et al. | |
| 2003/0215417 A1 | 11/2003 | Uchiyama | |
| 2003/0216488 A1 | 11/2003 | Uchiyama | |
| 2004/0071742 A1 | 4/2004 | Popplewell | |
| 2004/0071746 A1 | 4/2004 | Popplewell et al. | |
| 2004/0072719 A1 | 4/2004 | Bennett et al. | |
| 2004/0072720 A1 | 4/2004 | Brain et al. | |
| 2004/0087477 A1 | 5/2004 | Ness | |
| 2004/0106536 A1 | 6/2004 | Mane et al. | |
| 2005/0192204 A1 | 9/2005 | Trinh et al. | |
| 2007/0281880 A1 | 12/2007 | Morgan et al. | |
| 2009/0186096 A1 | 7/2009 | Kritzman et al. | |
| 2011/0268802 A1 | 11/2011 | Dihora | |
| 2012/0282309 A1 | 11/2012 | Dihora et al. | |
| 2013/0270267 A1 | 10/2013 | Ramsey et al. | |
| 2014/0178442 A1 | 6/2014 | Li et al. | |
| 2015/0132377 A1* | 5/2015 | Reymar | A61K 8/11 424/463 |
| 2015/0203787 A1 | 7/2015 | Lei et al. | |

(Continued)

FOREIGN PATENT DOCUMENTS

| | | |
|---|---|---|
| EP | 1393706 A1 | 3/2004 |
| EP | 1533364 B1 | 7/2008 |
| WO | 0180823 A2 | 11/2001 |

(Continued)

OTHER PUBLICATIONS

All Office Actions, U.S. Appl. No. 15/198,306.
All Office Actions, U.S. Appl. No. 15/198,234.
International Search Report and Written Opinion, dated Aug. 29, 2016, 12 pgs.
International Search Report and Written Opinion, dated Aug. 22, 2016, 12 pgs.
International Search Report and Written Opinion, dated Aug. 12, 2016, 21 pgs.

(Continued)

*Primary Examiner* — Celeste A Roney
(74) *Attorney, Agent, or Firm* — James E Oehlenschlager; Jason J Camp

(57) ABSTRACT

A method of making a consumer product providing multiple blooms of fragrance, the multiple blooms being provided for by different populations of microcapsules.

24 Claims, 1 Drawing Sheet

(56) References Cited

U.S. PATENT DOCUMENTS

2017/0002293 A1    1/2017    Dihora et al.
2017/0002301 A1    1/2017    Dihora et al.

FOREIGN PATENT DOCUMENTS

| WO | 2010/079467 A2 | 7/2010 |
| WO | 2010/084480 A2 | 7/2010 |
| WO | 2010079468 A2 | 7/2010 |
| WO | 2014029695 A1 | 2/2014 |
| WO | 2014047502 A2 | 3/2014 |
| WO | WO 2016/049389 A1 | 3/2016 |

OTHER PUBLICATIONS

Abedin, "Effect of Process Mixing on the Size Distribution and Mean Diameter of the Tliiol-triacrylate Micro Capsules", Louisiana State University and Agricultural and Mechanical College, 2014, 74 Pages.

Carlo Sofia, "Microencapsulation of Perfumes for Application in Textile Industry", Department of Chemical EngineeringFaculty of Engineering University of Porto, 2010, 246 Pages.

Neobee M-5 retrieved from https ://www. step an. com/ content/ stepan-dot-com/ en/products-markets/product/ NEOBEE on Dec. 7, 2020, 2 Pages.

Sesamol retrieved from https://de.wikipedia.org/wiki/Sesam%C3%B61 on Dec. 7, 2020, pp. 1-4.

Third Party Opposition filed for European Patent Application Serial No. 16739349.5, dated Apr. 29, 2020, 38 pages.

Third Party Opposition filed for European Patent Application Serial No. 16739349.5, dated May 6, 2020, 12 pages.

* cited by examiner

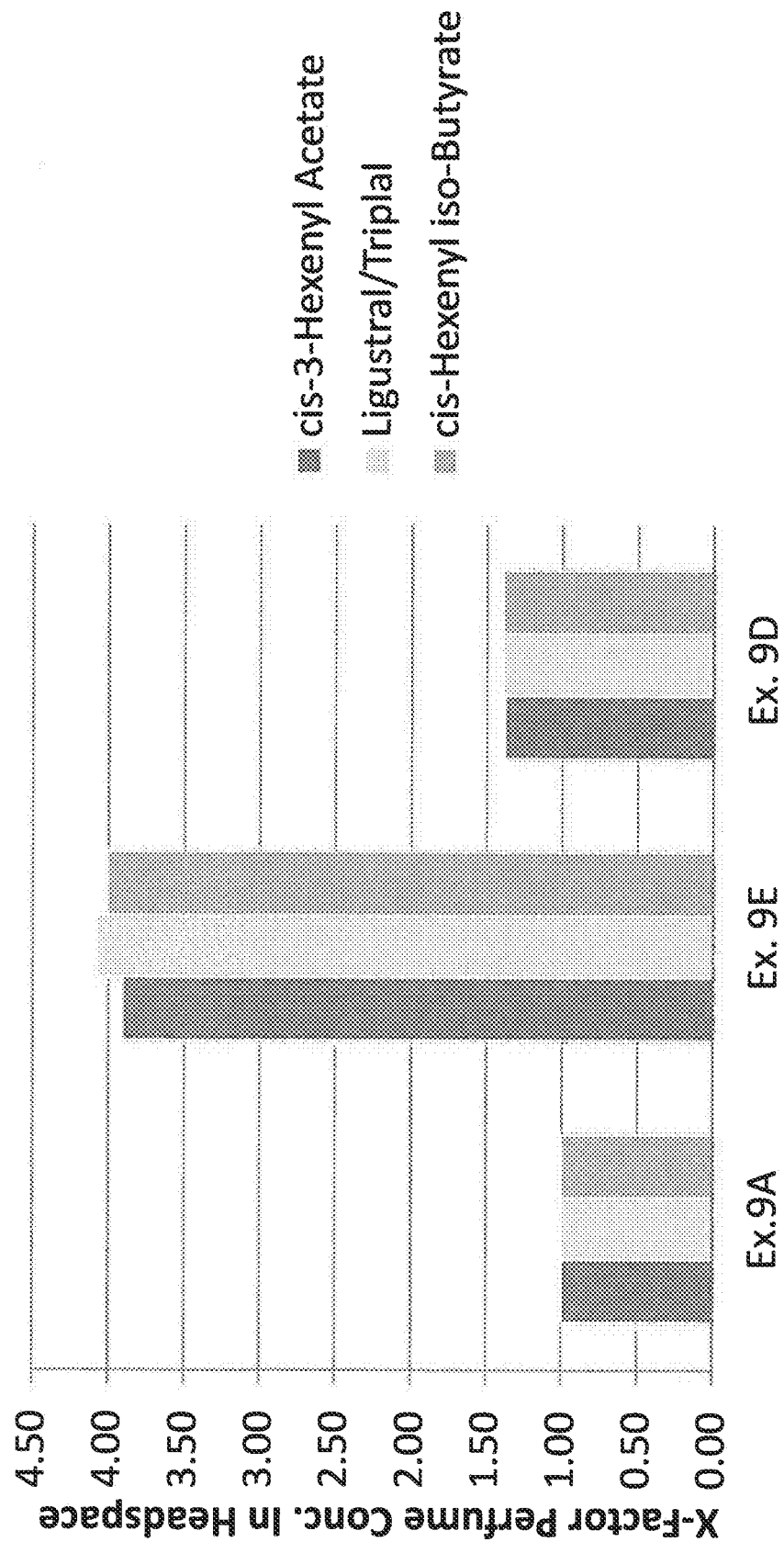

METHODS FOR MAKING COMPOSITIONS CONTAINING MULTIPLE POPULATIONS OF MICROCAPSULES

TECHNICAL FIELD

The present disclosure relates to methods of making compositions that provide multiple blooms of fragrances through the use of microcapsules.

BACKGROUND

Consumers often desire consumer products for the many benefits they may provide. For example, it is not uncommon for a particular consumer to have in their home shampoos, conditioners, body washes, deodorants, fine fragrances, shaving gels, etc. Often, such consumer products also include fragrances. Such fragrances may delight the user by providing a freshness feeling and may serve as a signal to the user that the product may still be working or that the product is still present. Yet because of the volatility of many fragrances and/or habituation, a consumer may be unable to notice the fragrance shortly after using/applying the consumer product, potentially leading the user to believe the benefits are dissipating or have dissipated. Consequentially, it may be desirable to have technologies than improve the noticeability of fragrances in consumer products.

SUMMARY

A method of making a consumer product that provides for multiple blooms of fragrance, the method comprising: combining a first adjunct material, a first population of microcapsules, and a second population of microcapsules to form the consumer product; wherein the first population has a first median volume weighted particle size and comprises microcapsules comprising a partitioning modifier and a first perfume oil at a first weight ratio; and wherein the second population of microcapsules has a second median volume weighted particle size and comprises microcapsules comprising the partitioning modifier and a second perfume oil at a second weight ratio; wherein the first and second weight ratio and/or the first and the second median volume weighted particle size are/is different.

BRIEF DESCRIPTION OF THE DRAWINGS

While the specification concludes with claims, it is believed that the same will be better understood from the following description taken in conjunction with the accompanying drawings in which:

FIG. 1 is a graph illustrating the concentration of perfume released into the headspace by leave-on conditioners containing microcapsules that vary in fragrance and fracture strength and that were applied to hair switches and combed 4 hours after application to the hair switches.

DETAILED DESCRIPTION

While the specification concludes with claims particularly pointing out and distinctly claiming the invention, it is believed that the present invention will be better understood from the following description.

All percentages, parts and ratios are based upon the total weight of the compositions of, unless otherwise specified. All such weights as they pertain to listed ingredients are based on the active level and, therefore do not include carriers or by-products that may be included in commercially available materials.

"Adjunct material" is any material that is not a microcapsule and that is added to the microcapsules to form the consumer product. The adjunct material may take many forms, and it is to be appreciated that an adjunct material may be a pure substance or include more than one type of material such that the adjunct material is collection/mixture of different materials, arranged in any manner Adjunct materials, however, are limited to those used in consumer products.

"Derivatives" as used herein, includes but is not limited to, amide, ether, ester, amino, carboxyl, acetyl, and/or alcohol derivatives of a given compound.

"Free of" means that the stated ingredient has not been added to the composition. However, the stated ingredient may incidentally form as a byproduct or a reaction product of the other components of the personal care composition.

"IPM" means isopropyl myristate.

"Mixtures" means to include a combination of materials in any combination.

"Molecular weight" or "M.Wt." as used herein refers to the weight average molecular weight unless otherwise stated.

"pH QS" means the amount required to adjust the pH accordingly.

"PMC" means a microcapsule having a shell and a core and wherein the core includes at least one perfume oil.

"PM" means partitioning modifier.

"PO" means perfume oil(s).

"QS" means the material is used to bring the total to 100%.

"Substantially free of" means an amount of a material that is less than 1%, 0.5%, 0.25%, 0.1%, 0.05%, 0.01%, or 0.001% by weight of a composition.

"Visc. QS" means the amount required to adjust the viscosity accordingly.

INTRODUCTION

The compositions described herein may deliver multiple blooms of fragrance to the consumer when used. Said compositions may comprise distinct populations of microcapsules as a way to deliver the multiple blooms of fragrance. It has surprisingly been found that including a first population of microcapsules and a second population of microcapsules where the first and second populations differ in fracture strengths may provide multiple blooms of fragrance. It has also been surprisingly found that varying the ratio of the partitioning modifier to the perfume oils within the core of the microcapsule can affect the fracture strength of the microcapsules even when the mass of the core material to the shell is relatively constant. Without being limited to theory, it is believed that the ratio of the partitioning modifier to the perfume oil may affect the plasticity/flexibility of the shell of the microcapsule, ultimately affecting the fracture strength of the microcapsule. By varying the ratio of the partitioning modifier to the perfume oil, microcapsules of different fracture strengths may be obtained. Furthermore, including populations of microcapsules with different fracture strength profiles may deliver multiple blooms, albeit with different kinetics.

The use of multiple distinct populations of microcapsules, each with a distinct bloom pattern, may be used to overcome the habituation experienced by some consumers to a fragrance present in an article and/or composition. In this regard, some consumers are known to suffer from habituation to the fragrance expressed by a composition and/or article such that the fragrance becomes less noticeable over time to the consumer. While methods of combating habituation are known, the practice of preventing habituation is no simple task and often requires delaying and/or triggering the release of the fragrances. For example, a method to combat habituation is to incorporate a non-encapsulated perfume oil and a different, encapsulated perfume oil into a composition and/or article. However in this case, habituation may still occur, while delayed, because the non-encapsulated perfume oil will likely possess a short half life and the consumer may become habituated to the encapsulated perfume oil once released. Moreover, while the encapsulated perfume oil may be released throughout the day, the consumer, once habituated to the encapsulated perfume oil, may cease to notice the release of the encapsulated perfume oil such that the consumer no longer enjoys the benefits provided by the encapsulation technology. In contrast, the incorporation of multiple populations of microcapsules into a composition/article, each with a distinct bloom pattern and fragrance profile, may help combat habituation to the encapsulation technology, and potentially allow the consumer to notice the fragrances throughout the period of use of the consumer product.

When manufacturing microcapsules for the encapsulation of oils, the properties inherent to the oil may play an important role in determining how much, how quickly, and how permeable the resultant shell material will be when established at the oil/water interface. For example, when the oil phase includes highly polar materials, such materials may reduce the diffusion of the monomers and polymers to the oil/water interface; potentially resulting in a relatively thin and highly permeable polymeric shell. Incorporating a partitioning modifier to adjust the polarity of the core may alter the partitioning coefficient of the polar materials, allowing for the establishment of a thicker, well defined shell. US Application 2011-0268802 provides several non-limiting examples of partitioning modifiers useful with oils and microcapsules and is hereby incorporated by reference.

Surprisingly, it has been discovered that while the presence of the partitioning modifier promotes shell formation, the weight ratio of the partitioning modifier to the perfume oil is not directly proportional to the shell thickness of the microcapsules. As shown in Table 1, the microcapsules of Example 1 were synthesized with varying ratios of isopropyl myristate (a partitioning modifier) to perfume oil. As shown in Table 1, when at least 10% isopropyl myristate is included, the shell thickness may be between 73-166 nm as compared to 10-15 nm in the absence of isopropyl myristate. Surprisingly however, increasing the level of isopropryl myristate in relation to the perfume oils beyond a weight ratio of 1:9 did not lead to a significant increase in the thickness of the shell. In this regard, the shell thickness varied from 73-166 nm when the weight ratio of isopropyl myristate to perfume oil is 1:9 while when the ratio of isopropyl myristate to perfume oil was 3:7 the shell thickness varied from 66-100 nm. Increasing the level of isopropryl myristate to perfume oil to a 1:1 ratio led to a reduction in the thickness of the shell, a reduction of from 73-166 nm to 30-70 nm. These data suggest that while the inclusion of a partitioning modifier may increase the thickness of the shell, increasing the ratio of the partitioning modifier to the perfume oil above 1:9 may not lead to a further increase in shell thickness.

TABLE 1

| % PM (IPM) | % PO | Weight Ratio of PM to PO | Shell Thickness (nm) |
| --- | --- | --- | --- |
| 0% | 100% | — | 10-15 |
| 10% | 90% | 1:9 | 73-166 |
| 20% | 80% | 1:4 | 80-115 |
| 30% | 70% | 3:7 | 66-100 |
| 40% | 60% | 2:3 | 115-122 |
| 50% | 50% | 1:1 | 30-70 |
| 87% | 13% | 7:1 | 19-45 |

Surprisingly, it has been discovered that in addition to promoting shell formation, the amount of the partitioning modifier relative to the perfume oil may also influence the fracture strength of the microcapsule independently of the shell thickness. As shown in Table 2, when the microcapsules are of similar sizes, the levels of partitioning modifier can strongly impact the fracture strength of the capsules. Comparing Example 1 to Example 2, increasing the amount of PM from 20% (Example 1) to 40% (Example 2) resulted in a drop in the fracture strength of from ~7.68 MPa to ~2.60 MPa, respectively.

As shown in Table 2, surprisingly, the size of the microcapsule may also impact the fracture strength of the microcapsule independently of the amount of the partitioning modifier present within the core of the microcapsule. Comparing Example 1 to Example 3, increasing the size of the microcapsule by about ~200% resulted in a ~395% decrease in the fracture strength. In this regard, Example 1 contained microcapsules with a median particle size of 12.6 microns while Example 3 contained microcapsules with a median particle size of 26.1 microns. Although the microcapsules of Example 1 and Example 3 contained about 20% PM within the core, the microcapsules of Example 1 exhibited a fracture strength of ~7.68 MPa while the microcapsules of Example 3 exhibited a fracture strength of ~1.94 MPa.

TABLE 2

| Example | Median PS μm | % PM | Fracture Strength (MPa) | Deformation at Fracture (%) |
| --- | --- | --- | --- | --- |
| 1 | 12.6 | 20 | 7.68 ± 2.0 | 51% ± 20% |
| 2 | 12.6 | 40 | 2.60 ± 1.2 | 37% ± 15% |
| 3 | 26.1 | 20 | 1.94 ± 1.2 | 30% ± 14% |
| 4 | 10 | 20 | 7.64 ± 2.2 | 56% ± 20% |

To determine whether the microcapsules of Examples 1-4 exhibited differences in their ability to release the encapsulated perfume oil upon exposure to normal human movements, the microcapsules were formulated into leave-on conditioners and tested for their abilities to fracture upon combing. The % of microcapsules fractured at each of the above events are displayed Table 3 below. Example 5 included the microcapsules of Example 1. Example 6 included the microcapsules of Example 2. Example 7 included the microcapsules of Example 3. Example 8 included the microcapsules of Example 4.

Examples 5-8 were applied to hair switches within 30 minutes of making in order to minimize the leakage of the perfume oil prior to application on the hair switches. The hair switches were allowed to dry at ambient temperature for 4 hours. The hair switches were then combed and the headspace values were obtained using the Headspace Method disclosed herein. The same hair switches were hung at ambient temperature, aged for 24 hours, and combed again, with the headspace value measured using the Headspace Method disclosed herein. Several controls were placed in the study to obtain a calibration curve for perfume on hair vs. perfume in the headspace. This calibration curve was utilized to calculate the % of capsules fractured at each combing event.

Comparing Example 5 to Example 6 in Table 3, about 14.5% of the microcapsules with a size of ~13 microns and a ratio of PM:PO of 2:3 fractured upon combing the hair switches 4 hours after application of the leave-on conditioner as compared to about 5.2% of microcapsules with a size of ~13 microns and a ratio of PM:PO of 1:4. Comparing Example 5 to Example 6 in Table 3, about 1.2% of the microcapsules with a size of ~12.6 microns and a ratio of PM:PO of 2:3 fractured after 24 hours of drying as compared to about 5.2% of microcapsules with a size of ~12/6 microns and a ratio of PM:PO of 1:4. These results suggest that varying the ratio of PM:PO can alter the fracture strength of the microcapsules, resulting in performance differences of the microcapsules when in a leave-on conditioner. In this regard, microcapsules with a higher fracture strength tend to release more perfume after 24 hours than microcapsules with a lower fracture strength. Additionally, microcapsules with a lower fracture strength tend to release more perfume after 4 hours than microcapsules with higher fracture strengths.

Interestingly, the size of the microcapsule also appeared to play a role in the amount of perfume released into the headspace, irrespective of the ratio of PM:PO. Comparing Example 7 to Example 6, although the fracture strengths of the microcapsules were not significantly different (~1.9 MPa vs. ~2.6 MPa, respectively), the microcapsules of Example 7 released significantly less perfume at 4 hours as compared to Example 5 (7.6 micrograms/gram vs 43.6 micrograms/gram). Additionally, while the microcapsules of Example 7 and Example 5 contained microcapsules with a similar ratio of PM:PO (i.e. 1:4), the microcapsules of Example 5 released a greater amount of perfume at 4 hours and 24 hours as compared to the microcapsules of Example 7. Altogether, these results suggest that modulating the ratio of PM:PO and the size of the microcapsule may have a profound effect on the release of perfume from the microcapsules when the microcapsules are provided in a consumer product.

Comparing Example 5 to Example 6, consumers rated hair switches with the leave-on conditioner of Example 6 a higher score than hair switches receiving the conditioner of Example 5 (i.e. a rating of 60 vs. 45). Additionally, it also appears that while Example 6 provided a more intense bloom of fragrance after 4 hours and 24 hours as compared to Example 5, consumers noticed a more intense bloom for Example 5 after 48 hours as compared to Example 6. These results suggest that varying the fracture strength of microcapsules of similar sizes may affect the bloom patterns of the microcapsules. In this regard, it appears that microcapsules with a lower fracture strength (e.g. ~2.6 MPa) may provide a more intense early bloom with a noticeable drop off in intensity while microcapsules with a higher fracture strength (~7.7 MPa) may deliver a more sustained bloom pattern. Interestingly, Example 8 which contained microcapsules of low fracture strength (e.g. ~1.9 MPa) and a high median particle size (e.g. 26 microns) appear to have a more diminished bloom over time as compared to Example 5 or Example 8. Thus it appears that increasing the median particle size of the microcapsules not only impacts the fracture strength of the microcapsules, but also appears to impact the bloom pattern of the perfume encapsulated. Lastly, these results also suggest that it may be possible to generate populations of microcapsules with different bloom patterns by adjusting the weight ratio of PM:PO within the core and/or by varying the median particle size of the microcapsule populations.

TABLE 4

|  | Example 5 | Example 6 | Example 7 | Example 8 |
| --- | --- | --- | --- | --- |
| Mean Particle Size; PM:PO weight ratio; Fracture Strength (MPa) | ~12.6 micron; 1:4; 7.7 ± 2.0 | ~12.6 micron; 2:3; 2.6 ± 1.2 | ~26 micron; 1:4; 1.9 ± 1.2 | ~10 micron; 1:4; 7.6 ± 2.2 |
| 4 hr Post-Comb | 45 | 60 | 45 | 50 |
| 24 hr Post-Comb | 45 | 55 | 45 | 50 |
| 48 hr Post-Comb | 40 | 35 | 30 | 50 |
| 72 hr Post-Comb | 40 | 35 | 35 | 45 |
| 96 hr Post-Comb | 40 | 30 | 35 | 45 |

TABLE 3

|  | Ex. 5 4 hr Results | Ex. 5 24 hr Results | Ex. 6 4 hr Results | Ex. 6 24 hr Results | Ex. 7 4 hr Results | Ex. 7 24 hr Results | Ex. 8 4 hr Results | Ex. 8 24 hr Results |
| --- | --- | --- | --- | --- | --- | --- | --- | --- |
| Mean Particle Size; PM:PO weight ratio; Fracture Strength (MPa) | ~12.6 micron; 1:4; 7.7 ± 2.0 | ~12.6 micron; 1:4; 7.7 ± 2.0 | ~12.6 micron; 2:3; 2.6 ± 1.2 | ~12.6 micron; 2:3; 2.6 ± 1.2 | ~26 micron; 1:4; 1.9 ± 1.2 | ~26 micron; 1:4; 1.9 ± 1.2 | ~10 micron; 1:4; 7.6 ± 2.2 | ~10 micron; 1:4; 7.6 ± 2.2 |
| Perfume (μg/g of hair) Released Upon Combing | 15.5 | 11.4 | 43.6 | 3.5 | 7.6 | 4.4 | 14.0 | 20.0 |
| % Capsules Fractured/ Combing Event | 5.2% | 3.8% | 14.5% | 1.2% | 2.5% | 1.5% | 4.7% | 6.7% |

To determine whether consumers could detect the differences in bloom among the microcapsules of Examples 1-4, the leave-on conditioners of Examples 5-8 were also used to treat hair switches that were then graded by a panel of consumers. The same hair switches were graded at 4 hr, 24 hr, 48 hr, 72 hr, and 96 hr after application of Examples 5-8. The results of this experiment are summarized in Table 4 below.

The observation that varying the weight ratio of PM:PO within the core of the microcapsules results in microcapsules with varying bloom patterns, led to the discovery that a consumer product may be generated with multiple, different populations of microcapsules in order to generate a consumer product with multiple blooms. In this regard, leave-on conditioners containing varying ratios of the microcapsules of Example 1 and Example 2, albeit with different encapsulated perfume oils (e.g. cis-3-hexenyl acetate, ligustral/ triplal, cis-hexenyl iso-butyrate) were prepared and evaluated for their fragrance bloom patterns over time. The products were applied to hair switches within 30 minutes of making using the Olfactive Analysis of Leave-on Treatment Product method. These hair switches were then allowed to dry at ambient temperature for 4 hours. The hair switches were combed at 4 hrs after application of the leave-on conditioner and the olfactive performance was evaluated by the headspace analysis method described herein.

As illustrated in FIG. 1, when the leave-on conditioner (Example 9E) contained microcapsules at a 2:1 ratio of the low fracture strength (Example 2) to the high fracture strengths microcapsules (Ex. 1), the microcapsules with a low fracture strength (~2.6 MPa) provided a strong perfume bloom initially (at or around 4 hours). At a 1:1 ratio of high to low fracture strength microcapsules, diminished the extent of the early bloom as compared to Example 9D. However, such a combination still produced a more pronounced bloom at 4 hours than Example 9A which only contained the high fracture strength microcapsules.

These results illustrate that the bloom profile of a consumer product may be customized to allow for different bloom patterns depending on the preferences of the formulator by simply varying the ratio of one population of microcapsules to the other(s). In some examples, if a more intense early bloom is desired (e.g. at 4 hours after application of the leave-on conditioner), then a higher ratio of the low fracture strength microcapsules to the high fracture strength microcapsules may be included in the consumer product. Because both the median particle size and the ratio of PM:PO influence the fracture strength of the microcapsules, distinct blooms of fragrance may be generated by incorporating populations of microcapsules that vary in the encapsulated perfume oil and in the ratio of PM:PO and/or median particle size. In some examples, if a longer lasting bloom is desired, a lower ratio of the low fracture strength microcapsules to the high fracture strength microcapsules may be included in the consumer product. In some examples, the formulator may incorporate distinct populations of microcapsules into the consumer product that vary not only in fracture strengths, but also in the type of perfume oil, in order to prevent habituation.

Microcapsules

The compositions/articles herein may include microcapsules. The microcapsules may be any kind of microcapsule disclosed herein or known in the art. The microcapsules may have a shell and a core material encapsulated by the shell. The core material of the microcapsules may include one or more perfume oils. The shells of the microcapsules may be made from synthetic polymeric materials or naturally-occurring polymers. Synthetic polymers may be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Natural polymers occur in nature and may often be extracted from natural materials. Non-limiting examples of naturally occurring polymers are silk, wool, gelatin, cellulose, proteins, and combinations thereof.

The microcapsules may be friable microcapsules. A friable microcapsule is configured to release its core material when its shell is ruptured. The rupture may be caused by forces applied to the shell during mechanical interactions. The microcapsules may have a shell with a volume weighted fracture strength of from about 0.1 mega Pascals to about 15.0 mega Pascals, when measured according to the Fracture Strength Test Method described herein, or any incremental value expressed in 0.1 mega Pascals in this range, or any range formed by any of these values for fracture strength. As an example, a microcapsule may have a shell with a volume weighted fracture strength of 0.8-15.0 mega Pascals (MPa), alternatively from 5.0-12.0 mega Pascals (MPa), or alternatively from 6.0-10.0 mega Pascals (MPa).

The microcapsules may have a median volume-weighted particle size of from 2 microns to 80 microns, from 10 microns to 30 microns, or from 10 microns to 20 microns, as determined by the Test Method for Determining Median Volume-Weighted Particle Size of Microcapsules described herein.

The microcapsules may have various core material to shell weight ratios. The microcapsules may have a core material to shell ratio that is greater than or equal to: 70% to 30%, 75% to 25%, 80% to 20%, 85% to 15%, 90% to 10%, and 95% to 5%.

The microcapsules may have shells made from any material in any size, shape, and configuration known in the art. Some or all of the shells may include a polyacrylate material, such as a polyacrylate random copolymer. For example, the polyacrylate random copolymer may have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, and the shell has an overall mass, the polyacrylate material may form 5-100% of the overall mass, or any integer value for percentage in this range, or any range formed by any of these values for percentage. As examples, the polyacrylate material may form at least 5%, at least 10%, at least 25%, at least 33%, at least 50%, at least 70%, or at least 90% of the overall mass.

Some or all of the microcapsules may have various shell thicknesses. For at least a first group of the provided microcapsules, each microcapsule may have a shell with an overall thickness of 1-300 nanometers, or any integer value for nanometers in this range, or any range formed by any of these values for thickness. As an example, microcapsules may have a shell with an overall thickness of 2-200 nanometers.

The microcapsules may also encapsulate one or more benefit agents. The benefit agent(s) include, but are not limited to, cooling sensates, warming sensates, perfume oils, oils, pigments, dyes, chromogens, phase change materials, and other kinds of benefit agent known in the art, in any combination. In some examples, the perfume oil encapsulated may have a ClogP of less than 4.5 or a ClogP of less than 4. Alternatively the perfume oil encapsulated may have a ClogP of less than 3. In some examples, the microcapsule may be anionic, cationic, zwitterionic, or have a neutral charge. The benefit agents(s) may be in the form of solids and/or liquids. The benefit agent(s) may be any kind of perfume oil(s) known in the art, in any combination.

The microcapsules may encapsulate a partitioning modifier in addition to the benefit agent. Non-limiting examples of partitioning modifiers include isopropyl myristate, mono-, di-, and tri-esters of $C_4$-$C_{24}$ fatty acids, castor oil, mineral oil, soybean oil, hexadecanoic acid, methyl ester isododecane, isoparaffin oil, polydimethylsiloxane, brominated vegetable oil, and combinations thereof. Microcapsules may also have varying ratios of the partitioning modifier to the benefit agent so as to make different populations of microcapsules that may have different bloom patterns. Such populations may also incorporate different perfume oils so as to make populations of microcapsules that display different bloom patterns and different scent experiences. US 2011-0268802 discloses other non-limiting examples of microcapsules and partitioning modifiers and is hereby incorporated by reference.

The microcapsule's shell may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules may include a core material and a shell surrounding the core material, wherein the shell comprises: a plurality of amine monomers selected from the group consisting of aminoalkyl acrylates, alkyl aminoalkyl acrylates, dialkyl aminoalykl acrylates, aminoalkyl methacrylates, alkylamino aminoalkyl methacrylates, dialkyl aminoalykl methacrylates, tertiarybutyl aminethyl methacrylates, diethylaminoethyl methacrylates, dimethylaminoethyl methacrylates, dipropylaminoethyl methacrylates, and mixtures thereof; and a plurality of multifunctional monomers or multifunctional oligomers. Non-limiting examples of emulsifiers include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates, palmitamidopropyltrimonium chloride (Varisoft PATC™, available from Degussa Evonik, Essen, Germany), distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate)methyl chloride quaternary salt, poly(l-vinylpyrrolidone-co-2-dimethyl aminoethyl methacrylate), poly(acryl amide-co-diallyldimethylammonium chloride), poly(allylamine), poly[bis(2-chloroethyl) ether-alt-1,3-bis[3-(dimethylamino)propyl]urea] quaternized, and poly(dimethylamine-co-epichlorohydrin-co-ethylenediamine), condensation products of aliphatic amines with alkylene oxide, quaternary ammonium compounds with a long-chain aliphatic radical, e.g. distearyldiammonium chloride, and fatty amines, alkyldimethylbenzylammonium halides, alkyldimethylethylammonium halides, polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(-hydroxypropyl methacrylate), poly(-ethyl-2-oxazoline), poly(2-isopropenyl-2-oxazoline-co-methyl methacrylate), poly(methyl vinyl ether), and polyvinyl alcohol-co-ethylene), and cocoamidopropyl betaine.

Process for making microcapsules are well known. Various processes for microencapsulation, and exemplary methods and materials, are set forth in U.S. Pat. Nos. 6,592,990; 2,730,456; 2,800,457; 2,800,458; 4,552,811; and US 2006/0263518 A1.

The microcapsule may be spray-dried to form spray-dried microcapsules. The composition may also contain one or more additional delivery systems for providing one or more benefit agents, in addition to the microcapsules. The additional delivery system(s) may differ in kind from the microcapsules. For example, wherein the microcapsule encapsulates a perfume oil, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), starch derivatives, and combinations thereof. Said polysaccharide material may or may not be modified.

The populations of microcapsules may include anionic, cationic, and non-ionic microcapsules, in any combination, when included in a composition with a pH range of from 2 to about 10, alternatively from about 3 to about 9, alternatively from about 4 to about 8.

The compositions may also include a parent fragrance and one or more encapsulated fragrances that may or may not differ from the parent fragrance. For example, the composition may include a parent fragrance and a non-parent fragrance. A parent fragrance refers to a fragrance that is dispersed throughout the composition and is typically not encapsulated when added to the composition. Herein, a non-parent fragrance refers to a fragrance that differs from a parent fragrance included within the composition and is encapsulated with an encapsulating material prior to inclusion into the composition. Non-limiting examples of differences between a fragrance and a non-parent fragrance include differences in chemical make-up.

The populations of microcapsules may include anionic, cationic, and non-ionic microcapsules, in any combination, when included in a composition with a pH range of from 2 to about 10, alternatively from about 3 to about 9, alternatively from about 4 to about 8.

In some examples, the populations of microcapsules have different shell chemistries. As a non-limiting example, a composition may include a first population of microcapulses having a polyacrylate shell and a second population of microcapsules including a resorcinol shell.

In some examples, the microcapsules may include a benefit agent comprising: a.) a perfume composition having a Clog P of less than 4.5; b.) a perfume composition comprising, based on total perfume composition weight, 60% perfume materials having a Clog P of less than 4.0; c.) a perfume composition comprising, based on total perfume composition weight, 35% perfume materials having a Clog P of less than 3.5; d.) a perfume composition comprising, based on total perfume composition weight, 40% perfume materials having a Clog P of less than 4.0 and at least 1% perfume materials having a Clog P of less than 2.0; e.) a perfume composition comprising, based on total perfume composition weight, 40% perfume materials having a Clog P of less than 4.0 and at least 15% perfume materials having a Clog P of less than 3.0; f.) a perfume composition comprising, based on total perfume composition weight, at least 1% butanoate esters and at least 1% of pentanoate esters; g.) a perfume composition comprising, based on total perfume composition weight, at least 2% of an ester comprising an allyl moiety and at least 10% of another perfume comprising an ester moiety; h.) a perfume composition comprising, based on total perfume composition weight, at least 1% of an aldehyde comprising an alkyl chain moiety; i.) a perfume composition comprising, based on total perfume composition weight, at least 2% of a butanoate ester; j.) a perfume composition comprising, based on total perfume composition weight, at least 1% of a pentanoate ester; k.) a perfume composition comprising, based on total perfume composition weight, at least 3% of an ester comprising an allyl moiety and 1% of an aldehyde comprising an alkyl chain moiety; l.) a perfume composition comprising, based on total perfume composition weight, at least 25% of a perfume comprising an ester moiety and 1% of an aldehyde comprising an alkyl chain moiety; m.) a perfume compositions comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one, 3-methyl-4-(2,6,6-trimethyl-1-cyclohexen-2-yl)- and mixtures thereof; n.) a perfume composition comprising, based on total perfume composition weight, at least 0.1% of tridec-2-enonitrile, and mandaril, and mixtures thereof; o.) a perfume composition comprising, based on total perfume composition weight, at least 2% of a material selected from 3,7-dimethyl-6-octene nitrile, 2-cyclohexylidene-2-phenylacetonitrile and mixtures thereof; p.) a perfume composition comprising, based on total perfume composition weight, at least 80% of one or more perfumes comprising a moiety selected from the group consisting of esters, aldehydes, ionones, nitriles, ketones and combinations thereof; q.) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhexyl-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid, 3-(1-methylethyl)-ethyl ester; bycyclo[2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2 (3h)-furanone; 1,6-nonadien-3-ol, 3,7dimethyl-; 3,7-dimethylocta-1,6-dien-3-o; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle[5.2.1.0]decan-2-carboxylate; 2,2-dimethyl-cyclohexanepropanol; hexyl ethanoate, 7-acetyl, 1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol, 2-methyl-6-methylene-,dihydro; cyclohexanol, 2-(1,1-dimethylethyl)-, acetate; hexahydro-4,7-methanoinden-5(6)-yl propionatehexahydro-4,7-methanoinden-5 (6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one, 3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof; r.) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid, 3-(1-methylethyl)-ethyl ester; bycyclo[2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate, 4-undecanolide; 5-heptyldihydro-2(3h)-furanone; 5-hydroxydodecanoic acid; decalactones; undecalactones, 1,6-nonadien-3-ol, 3,7dimethyl-; 3,7-dimethylocta-1,6-dien-3-ol; 3-cyclohexene-1-carboxaldehyde, dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle[5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol, 2-methyl-6-methylene-,dihydro, cyclohexanol, 2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one, 3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-0-methylhydrocinnamaldehyde; ethyl-2,4-hexadienoate; 2-propenyl 3-cyclohexanepropanoate; and mixtures thereof; s.) a perfume composition comprising, based on total perfume composition weight, at least 5% of a material selected from the group consisting of 3-cyclohexene-1-carboxaldehyde, dimethyl-; 3-buten-2-one, 3-methyl-4-(2,6,6-trimethyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof; t.) a perfume composition comprising, based on total perfume composition weight, less than 10% perfumes having a Clog P greater than 5.0; u.) a perfume composition comprising geranyl palmitate; or v.) a perfume composition comprising a first and an optional second material, said first material having: (i) a Clog P of at least 2; (ii) a boiling point of less than about 280° C.; and second optional second material, when present, having (i) a Clog P of less than 2.5; and (ii) a ODT of less than about 100 ppb.

In some examples, the microcapsules may include a benefit agent comprising: one or more materials selected from the group consisting of (5-methyl-2-propan-2-ylcyclohexyl)acetate; 3,7-dimethyloct-6-en-1-al; 2-(phenoxy)ethyl 2-methylpropanoate; prop-2-enyl 2-(3-methylbutoxy)acetate; 3-methyl-1-isobutylbutyl acetate; prop-2-enyl hexanoate; prop-2-enyl 3-cyclohexylpropanoate; prop-2-enyl heptanoate; (E)-1-(2,6,6-trimethyl-1-cyclohex-2-enyl) but-2-en-1-one; (E)-4-(2,6,6-trimethyl-1-cyclohex-2-enyl) but-3-en-2-one; (E)-3-methyl-4-(2,6,6-trimethyl-1-cyclohex-2-enyl)but-3-en-2-one; 1-(2,6,6-trimethyl-1-cyclohex-2-enyl)pent-1-en-3-one; 6,6,9a-trimethyl-1,2,3a,4,5,5a,7,8,9,9b-decahydronaphtho[2,1-b]furan; pentyl 2-hydroxybenzoate; 7,7-dimethyl-2-methylidene-norbornane; (E)-1-(2,6,6-trimethyl-1-cyclohexenyl)but-2-en-1-one; (E)-4-(2,6,6-trimethyl-1-cyclohexenyl)but-3-en-2-one; 4-ethoxy-4,8,8-trimethyl-9-methylidenebicyclo[3.3.1] nonane; (1,7,7-trimethyl-6-bicyclo[2.2.1]heptanyl)acetate; 3-(4-tert-butylphenyl)propanal; 1,1,2,3,3-pentamethyl-2,5,6,7-tetrahydroinden-4-one; 2-oxabicyclo2.2.2octane, 1methyl4(2,2,3trimethylcyclopentyl); [(Z)-hex-3-enyl]acetate; [(Z)-hex-3-enyl]2-methylbutanoate; cis-3-hexenyl 2-hydroxybenzoate; 3,7-dimethylocta-2,6-dienal; 3,7-dimethyloct-6-en-1-al; 3,7-dimethyl-6-octen-1-ol; 3,7-dimethyloct-6-enyl acetate; 3,7-dimethyloct-6-enenitrile; 2-(3,7-dimethyloct-6-enoxy)acetaldehyde; tetrahydro-4-methyl-2-propyl-2h-pyran-4-yl acetate; ethyl 3-phenyloxirane-2-carboxylate; hexahydro-4,7-methano-indenyl isobutyrate; 2,4-dimethylcyclohex-3-ene-1-carbaldehyde; hexahydro-4,7-methano-indenyl propionate; 2-cyclohexylethyl acetate; 2-pentylcyclopentan-1-ol; (2R,3R,4S,5S,6R)-2-[(2R,3S,4R,5R,6R)-6-(6-cyclohexylhexoxy)-4,5-dihydroxy-2-(hydroxymethyl)oxan-3-yl]oxy-6-(hydroxymethyl)oxane-3,4,5-triol; (E)-1-(2,6,6-trimethyl-1-cyclohexa-1,3-dienyl)but-2-en-1-one; 1-cyclohexylethyl(E)-but-2-enoate; dodecanal; (E)-1-(2,6,6-trimethyl-1-cyclohex-3-enyl)but-2-en-1-one; (5E)-3-methylcyclopentadec-5-en-1-one; 4-(2,6,6-trimethyl-1-cyclohex-2-enyl)butan-2-one; 2-methoxy-4-propylphenol; methyl 2-hexyl-3-oxocyclopentane-1-carboxylate; 2,6-dimethyloct-7-en-2-ol; 4,7-dimethyloct-6-en-3-one; 4-(octahydro-4,7-methano-5H-inden-5-yliden)butanal; acetaldehyde ethyl linalyl acetal; ethyl 3,7-dimethyl-2,6-octadienoate; ethyl 2,6,6-trimethylcyclohexa-1,3-diene-1-carboxylate; 2-ethylhexanoate; (6E)-3,7-dimethylnona-1,6-dien-3-ol; ethyl 2-methylbutanoate; ethyl 2-methylpentanoate; ethyl tetradecanoate; ethyl nonanoate; ethyl 3-phenyloxirane-2-carboxylate; 1,4-dioxacycloheptadecane-5,17-dione; 1,3,3-trimethyl-2-oxabicyclo[2,2,2]octane; [essential oil]; oxacyclo-hexadecan-2-one; 3-(4-ethylphenyl)-2,2-dimethylpropanal; 2-butan-2-ylcyclohexan-1-one; 1,4-cyclohexandicarboxylic acid, diethyl ester; (3 aalpha, 4beta, 7beta, 7 aalpha)-octahydro-4,7-methano-3 aH-indene-3a-carboxylic acid ethyl ester; hexahydro-4-7, menthano-1H-inden-6-yl propionate; 2-butenon-1-one, 1-(2,6-dimethyl-6-methylencyclohexyl)-; (E)-4-(2,2-dimethyl-6-methylidenecyclohexyl)but-3-en-2-one; 1-methyl-4-propan-2-ylcyclohexa-1,4-diene; 5-heptyloxolan-2-one; 3,7-dimethylocta-2,6-dien-1-ol; [(2E)-3,7-dimethylocta-2,6-dienyl]acetate; [(2E)-3,7-dimethylocta-2,6-dienyl] octanoate; ethyl 2-ethyl-6,6-dimethylcyclohex-2-ene-1-carboxylate; (4-methyl-1-propan-2-yl-1-cyclohex-2-enyl) acetate; 2-butyl-4,6-dimethyl-5,6-dihydro-2H-pyran; oxacyclohexadecen-2-one; 1-propanol,2-[1-(3,3-dimethylcyclohexyl)thoxy]-2-methyl-propanoate; 1-heptyl acetate; 1-hexyl acetate; hexyl 2-methylpropanoate; (2-(1-ethoxyethoxy)ethyl)benzene; 4,4a,5,9b-tetrahydroindeno[1,2-d][1,3]dioxine; undec-10-enal; 3-methyl-4-(2,6,6-trimethyl-2-cyclohexen-1-yl)-3-buten-2-one; 1-(1,2,3,4,5,6,7,8-octahydro-2,3,8,8-tetramethyl-2-naphthalenyl)-ethan-1-one; 7-acetyl, 1,2,3,4,5,6,7-octahydro-1,1,6,7,-tetra methyl naphthalene; 3-methylbutyl 2-hydroxybenzoate; [(1R,4S,6R)-1,7,7-trimethyl-6-bicyclo[2.2.1]heptanyl]acetate; [(1R,4R,6R)-1,7,7-trimethyl-6-bicyclo[2.2.1]heptanyl]2-methylpropanoate; (1,7,7-trimethyl-5-bicyclo[2.2.1]heptanyl) propanoate; 2-methylpropyl hexanoate; [2-methoxy-4-[(E)-prop-1-enyl]phenyl]acetate; 2-hexylcyclopent-2-en-1-one; 5-methyl-2-propan-2-ylcyclohexan-1-one; 7-methyloctyl acetate; propan-2-yl 2-methylbutanoate; 3,4,5,6,6-pentamethylheptenone-2; hexahydro-3,6-dimethyl-2(3H)-benzofuranone; 2,4,4,7-tetramethyl-6,8-nonadiene-3-one oxime; dodecyl acetate; [essential oil]; 3,7-dimethylnona-2,6-dienenitrile; [(Z)-hex-3-enyl]methyl carbonate; 2-methyl-3-(4-tert-butylphenyl)propanal; 3,7-dimethylocta-1,6-dien-3-ol; 3,7-dimethylocta-1,6-dien-3-yl acetate; 3,7-dimethylocta-1,6-dien-3-yl butanoate; 3,7-dimethylocta-1,6-dien-3-yl formate; 3,7-dimethylocta-1,6-dien-3-yl 2-methylpropanoate; 3,7-dimethylocta-1,6-dien-3-yl propanoate; 3-methyl-7-propan-2-ylbicyclo[2.2.2]oct-2-ene-5-carbaldehyde; 2,2-dimethyl-3-(3-methylphenyl)propan-1-ol; 3-(4-tert-butylphenyl)butanal; 2,6-dimethylhept-5-enal; 5-methyl-2-propan-2-yl-cyclohexan-1-ol; 1-(2,6,6-trimethyl-1-cyclohexenyl)pent-1-en-3-one; methyl 3-oxo-2-pentylcyclopentaneacetate; methyl tetradecanoate; 2-methylundec anal; 2-methyldecanal; 1,1-dimethoxy-2,2,5-trimethyl-4-hexene; [(1S)-3-(4-methylpent-3-enyl)-1-cyclohex-3-enyl]methyl acetate; 2-(2-(4-methyl-3-cyclohexen-1-yl) propyl)cyclo-pentanone; 4-penten-1-one, 1-(5,5-dimethyl-1-cyclohexen-1-yl; 1H-indene-ar-propana1,2,3,-dihydro-1,1-dimethyl-(9CI); 2-ethoxynaphthalene; nonanal; 2-(7,7-dimethyl-4-bicyclo[3.1.1]hept-3-enyl)ethyl acetate; octanal; 4-(1-methoxy-1-methylethyl)-1-methylcyclohexene; (2-tert-butylcyclohexyl)acetate; (E)-1-ethoxy-4-(2-methylbutan-2-yl)cyclohexane; 1,1-dimethoxynon-2-yne; [essential oil]; 2-cyclohexylidene-2-phenylacetonitrile; 2-cyclohexyl-1,6-heptadien-3-one; 4-cyclohexyl-2-methylbutan-2-ol; 2-phenylethyl 2-phenylacetate; (2E,5E/Z)-5,6,7-trimethyl octa-2,5-dien-4-one; 1-methyl-3-(4-methylpent-3-enyl)cyclohex-3-ene-1-carbaldehyde; methyl 2,2-dimethyl-6-methylidenecyclohexane-1-carboxylate; 1-(3,3-dimethylcyclohexyl)ethyl acetate; 4-methyl-2-(2-methylprop-1-enyl)oxane; 1-spiro(4.5)-7-dec en-7-yl-4-penten-1-one; 4-(2-butenylidene)-3,5,5-trimethylcyclohex-2-en-1-one; 2-(4-methyl-1-cyclohex-3-enyl)propan-2-ol; 4-isopropylidene-1-methyl-cyclohexene; 2-(4-methyl-1-cyclohex-3-enyl)propan-2-yl acetate; 3,7-dimethyloctan-3-ol; 3,7-dimethyloctan-3-ol; 3,7-dimethyloctan-3-yl acetate; 3-phenylbutanal; (2,5-dimethyl-4-oxofuran-3-yl)acetate; 4-methyl-3-decen-5-ol; undec-10-enal; (4-formyl-2-methoxyphenyl) 2-methylpropanoate; 2,2,5-trimethyl-5-pentylcyclopentan-1-one; 2-tert-butylcyclohexan-1-ol; (2-tert-butylcyclohexyl)acetate; 4-tert-butylcyclohexyl acetate; 1-(3-methyl-7-propan-2-yl-6-bicyclo[2.2.2]oct-3-enyl)ethanone; (4,8-dimethyl-2-propan-2-ylidene-3,3a,4,5,6,8a-hexahydro-1H-azulen-6-yl)acetate; [(4Z)-1-cyclooct-4-enyl]methyl carbonate; methyl beta naphtyl ether; materials and stereoisomers thereof.

In some examples, the microcapsules may be resorcinol capsules. In some examples, a method for manufacturing a solid composition, selected from the group consisting of (a) by mixing a microcapsule dispersion comprising microcapsules, the capsule walls of which contain a resin which may be obtained by reacting:

(i) at least one aromatic alcohol or its ether or derivatives with
(ii) at least one aldehydic component that has at least two C atoms per molecule, and
(iii) optionally in the presence of at least one (meth) acrylate polymer into a solid composition;
(b) by mixing said microcapsules in granulated or supported form into a solid composition;
or
(c) by mixing said microcapsules in dried form into the solid composition is disclosed.

The microcapsules contain, in particular, liquids, comprising:
i. aromatic substances (perfume oils)
ii. liquid detergent and cleaning agent ingredients, such as, preferably, surfactants, in particular nonionic surfactants, silicone oils, paraffins
iii liquid non-pharmaceutical additives or active substances, for example oils such as, for example, almond oil or cooling substances, and
mixtures of the above.

The microcapsules may be manufactured by combining and reacting together, optionally in the presence of at least one (meth)acrylate polymer and if necessary in the presence of at least one substance to be encapsulated (the core material), the at least one aromatic alcohol to be reacted and the at least one aldehydic component having at least two C atoms per molecule to be reacted, and by subsequently hardening the capsules by increasing the temperature. In so doing, it is particularly preferred that the pH is increased over the course of the process.

During such a process, preferably first
(a) the at least one aromatic alcohol and/or its derivative or ether and the at least one aldehydic component and, optionally, at least one (meth)acrylate polymer and at least one substance to be encapsulated are combined at a temperature of 40 to 65° C. and a pH between 6 and 9, preferably 7 and 8.5, and
(b) in a later method step the pH is raised at a temperature of 40 to 65° C. to more than 9, preferably between 9.5 and 11,
(c) the capsules later being hardened by increasing the temperature to 60° C. up to 110° C., preferably 70° C. up to 90° C., in particular 80° C.

However, if phloroglucin is used as the alcohol component, it is more advantageous to harden the capsules in the acidic range; preferably the pH is then no higher than 4, particularly preferably between 3 and 4, for example between 3.2 and 3.5.

The yield and quality of the microcapsules or microcapsule dispersions that may be used are influenced by the chosen parameters of temperature, pH and/or stirring speed. In particular, a too-low temperature can lead to a less-thick capsule wall. This is apparent to the person skilled in the art in a reduced yield as well as precipitation of core material as condensate in the filter of the dryer. On the other hand, it should be made sure that the reaction speed is not too high, because otherwise there will be only a little wall material around the capsules or there will be too much free wall material outside the capsules. This free wall material may then be present in particles that are larger than the capsules.

Alkalinity can also be important for the quality of the microcapsules that can be used. In addition, within the scope of process control, the pH influences the tendency of the preparation to gel. If particles are formed (step (b), above) at a pH of 9 or lower, the preparation could gel. In some examples, an alkali salt, preferably alkali carbonate, in particular sodium carbonate, is used to adjust the alkalinity. Sodium carbonate is preferred because it reduces the risk of gelling.

Compositions/Articles

The compositions may be packaged in any package known in the art and sold as consumer products (i.e. products intended to be sold to consumers without further modification or processing). Moreover, the spray-dried microcapsules may be applied to any article, such as a fabric or any absorbent material including, but not limited to, feminine hygiene products, diapers, and adult incontinence products. The composition may also be incorporated into an article, non-limiting examples of which include a dispenser/container. The compositions/articles disclosed herein may be made by combining the populations of microcapsules disclosed herein with the desired adjunct material to form the consumer product. The microcapsules may be combined with the adjunct material when the microcapsules are in one or more forms, including a slurry form, neat particle form, and spray dried particle form. The microcapsules may be combined with the adjunct material by methods that include mixing and/or spraying.

In some examples of consumer products, the microcapsules may consist of one or more distinct populations. The consumer product may have at least two different populations of microcapsules that vary in the exact make up the perfume oil and in the median particle size and/or PM:PO weight ratio. In some examples, the consumer product includes more than two distinct populations that vary in the exact make up the perfume oil and in their fracture strengths. In some examples, the populations of microcapsules vary with respect to the weight ratio of the partitioning modifier to the perfume oil(s). In some examples, the consumer product includes a first population of microcapsules having a first ratio that is a weight ratio of from 2:3 to 3:2 of the partitioning modifier to a first perfume oil and a second population of microcapsules having a second ratio that is a weight ratio of less than 2:3 but greater than 0 of the partitioning modifier to the second perfume oil. In some examples, the weight ratio of the first population of microcapsules to the second population of microcapsules is less than 1:1 but greater than 0. In some examples, the weight ratio of first population of microcapsules to the second population of microcapsules exceeds 1:1.

In some examples, each distinct population of microcapsules is prepared in a distinct slurry. In some examples, the first population of microcapsules is contained in a first slurry and the second population of microcapsules is contained in a second slurry. It is to be appreciated that the number of distinct slurries for combination is without limit and a choice of the formulator such that 3, 10, or 15 distinct slurries may be combined. The first and second populations of microcapsules may vary in the exact make up the perfume oil and in the median particle size and/or PM:PO weight ratio. In some examples, the consumer product, is prepared by combining the first and second slurries with at least one adjunct ingredient and optionally packaged in a container. In some examples, the first and second populations of microcapsules are prepared in distinct slurries and then spray dried. The distinct slurries may be combined before spray drying, or spray dried individually and then combined together when in powder form. Once in powder form, the first and second populations of microcapsules may be combined with an adjunct ingredient to form the consumer product. In some examples, at least one population of microcapsules is spray dried and combined with a slurry of a second population of microcapsules. In some examples, at least one population of microcapsules is dried, prepared by spray drying, fluid bed drying, tray drying, or other such drying processes that are available.

In some examples, said slurry includes one or more processing aids selected from the group consisting of a carrier, an aggregate inhibiting material, a deposition aid, a particle suspending polymer, and mixtures thereof. Non-limiting examples of aggregate inhibiting materials include salts that can have a charge-shielding effect around the particle, such as magnesium chloride, calcium chloride, magnesium bromide, magnesium sulfate, and mixtures thereof. Non-limiting examples of particle suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

In some examples, said slurry includes one or more processing aids, selected from the group consisting of water, aggregate inhibiting materials such as divalent salts; particle suspending polymers such as xanthan gum, guar gum, caboxy methyl cellulose.

In some examples, the slurry includes one or more carriers selected from the group consisting of polar solvents, including but not limited to, water, ethylene glycol, propylene glycol, polyethylene glycol, glycerol; nonpolar solvents, including but not limited to, mineral oil, perfume raw materials, silicone oils, hydrocarbon paraffin oils, and mixtures thereof.

In some examples, said slurry may include a deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, polyvinyl alcohol; polyvinyl alcohol crosslinked with boric acid; polyacrylic acid; polyglycerol ether silicone crosspolymers; polyacrylic acids, polyacrylates, copolymers of polyvinylamine and polvyinylalcohol oligimers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimime, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof.

In some examples, at least one population of microcapsules is contained in an agglomerate and then combined with a distinct population of microcapsules and at least one adjunct material. Said agglomerate may comprise materials selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

The different populations of microcapsules may be formulated into any suitable form and prepared by any process chosen by the formulator, non-limiting examples of which are described in U.S. Pat. No. 5,879,584 which is incorporated herein by reference.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Non-limiting examples of consumer products useful herein include products for treating hair (human, dog, and/or cat), including, bleaching, coloring, dyeing, conditioning, growing, removing, retarding growth, shampooing, styling; deodorants and antiperspirants; personal cleansing; color cosmetics; products, and/or methods relating to treating skin (human, dog, and/or cat), including application of creams, lotions, and other topically applied products for consumer use; and products and/or methods relating to orally administered materials for enhancing the appearance of hair, skin, and/or nails (human, dog, and/or cat); shaving; body sprays; and fine fragrances like colognes and perfumes; products for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps, shampoos, lotions, oral care implements, and clothing; products such as wet or dry bath tissue, facial tissue, disposable handkerchiefs, disposable towels, and/or wipes; products relating to catamenial pads, incontinence pads, interlabial pads, panty liners, pessaries, sanitary napkins, tampons and tampon applicators, and/or wipes.

Personal Care Compositions

In some examples, the consumer product may be a personal care composition, that is, a composition intended to be applied anywhere on the human body for any period of time. Non-limiting examples of personal care compositions include products such as those intended to treat and/or clean hair, styling products, deodorants and antiperspirants, personal cleansing products, cosmetics products, product relating to treating skin such as creams, lotions, and other topically applied products for consumer use; shaving products; body sprays; and fine fragrances like colognes and perfumes. The personal care compositions may be manufactured by any method known in the art and packaged in any dispenser known in the art. In some examples, the personal care composition may include at least two populations of microcapsules and one or more adjunct materials. Some non-limiting examples of personal care compositions are described in further detail below. In some examples, the personal care composition may include from about 0.01% to about 20%, by weight of the personal care composition, of microcapsules.

Shampoo Composition

The shampoo compositions described herein may comprise from about 0.025% to about 20%, alternatively from about 0.05% to about 0.5%, alternatively from about 0.1% to about 1% microcapsules, by weight of the shampoo composition. After applying to the hair a shampoo composition as described herein, the method may then comprise rinsing the shampoo composition from the hair.

The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %. The shampoo composition may also comprise a shampoo gel matrix, an aqueous carrier, and other additional ingredients described herein.

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

The shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable. The shampoo gel matrix surfactants may be a detersive surfactant.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Conditioner Composition

The conditioner compositions described herein comprise (i) from about 0.025% to about 20%, alternatively from about 0.05% to about 0.5%, alternatively from about 0.1% to about 1% microcapsules, by weight of the conditioner composition, and (ii) a conditioner gel matrix. After applying to the hair a conditioner composition as described herein, the method then comprises rinsing the conditioner composition from the hair. The conditioner composition also comprises a conditioner gel matrix comprising (1) one or more high melting point fatty compounds, (2) a cationic surfactant system, and (3) a second aqueous carrier.

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-On Treatment

The leave-on treatment described herein may comprise from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment. The leave-on treatment also comprises (1) one or more rheology modifiers and (2) a third aqueous carrier. The leave-on treatment may also include from about 0.025% to about 20%, alternatively from about 0.05% to about 0.5%, alternatively from about 0.1% to about 1% microcapsules, by weight of the leave-on treatment.

The leave-on treatment may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. In some examples, the leave-on treatment may comprise from about 0.01% to about 3% of a rheology modifier, alternatively from about 0.1% to about 1% of a rheology modifier, The leave-on treatment may comprise a third aqueous carrier. Accordingly, the formulations of the leave-on treatment can be in the form of pourable liquids (under ambient conditions). Such compositions will therefore typically comprise a third aqueous carrier, which is present at a level of at least 20 wt %, from about 20 wt % to about 95 wt %, or from about 60 wt % to about 85 wt %. The third aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The third aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

pH

The shampoo composition, conditioner composition, and/or leave-on treatment may have a pH in the range from about 2 to about 10, at 25° C. The shampoo composition, conditioner composition, and/or leave-on treatment may have a pH in the range of from about 2 to about 6, alternatively from about 3.5 to about 5, alternatively from about 5.25 to about 7, which may help to solubilize copper and redox metals already deposited on the hair.

Additional Components

The shampoo composition, conditioner composition, and/or leave-on treatment (hair care compositions) described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents (e.g., silicones, hydrocarbon oils, fatty esters), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

Rinse-Off Formulations

The personal care composition may be a rinse-off formulation that can be applied topically to the skin and/or hair and rinsed from the skin and/or hair within minutes with water. The personal care composition may comprise a primary surfactant. Primary surfactants may comprise from 0.1% to 20%, from about 2% to about 10%, from about 5% to about 10%, or from about 2% to about 5% by weight of the personal care composition. The primary surfactant may comprise one or more anionic surfactants. The personal care compositions may also comprise a secondary surfactant. Secondary surfactants may comprise from 0.1% to 20%, from about 2% to about 10%, or from about 2% to about 5% by weight of the personal care composition. Secondary surfactants may also comprise more than 20% by weight of the personal care composition. The personal care compositions may also contain from about 20% to about 95%, from about 40% to about 90%, from about 60% to about 90%, or from about 70% to about 90% of water, by weight of the personal care composition. The personal care compositions may further comprise a viscosity modifier for modifying the viscosity of the personal care composition. Such concentrations of viscosity modifiers may range, for example, from about 0.1% to about 10%, from about 0.3% to about 5.0%, from about 0.5% to about 10%, or from 0.5% to 3% by weight of the personal care compositions. The personal care compositions may also include other personal care adjunct ingredients that may modify the physical, chemical, cosmetic or aesthetic characteristics of the personal care compositions or serve as "active" components when deposited on the skin. Non-limiting examples of primary surfactants include sodium lauryl sulfate, ammonium lauryl sulfate, sodium laureth sulfate, and ammonium laureth sulfate. Non-limiting examples of secondary surfactants include cocamidopropyl betaine. Non-limiting examples of other ingredients include fragrances and polyols. Non-limiting examples of viscosity modifiers include sodium carbonate, sodium chloride, sodium aluminum sulfate, disodium phosphate, sodium polymetaphosphate, sodium magnesium succinate, sodium sulfate, sodium tripolyphosphate, aluminum sulfate, aluminum chloride.

The rinse-off formulation may be a single-phased or a multi-phased product. Multi-phased is meant that at least two phases herein occupy separate, but distinct physical spaces inside the package in which they are stored, but are in direct contact, with another. The multi-phase product may have a cleansing phase and a benefit phase. The cleansing phase may comprise a surfactant component comprising a surfactant or a mixture of surfactants. Non-limiting examples of these surfactants include anionic, nonionic, cationic, zwitterionic, and amphoteric surfactants, soap, and combinations thereof. The benefit phase may be anhydrous. The multi-phase product may also include a non-lathering, structured aqueous phase that comprises a water structurant and water. The single and/or multi-phase product may also include other ingredients, non-limiting examples of which include humectants, occlusive agents, and fragrances.

Body Spray/Fine Fragrance

The personal care composition may be an aerosolized composition like a body spray and fine fragrance. The aerosolized compositions described herein may include a volatile solvent or a mixture of volatile solvents. The volatile solvents may comprise greater than or equal to 10%, greater than 30%, greater than 40%, greater than 50%, greater than 60%, or greater than 90%, and less than 99% by weight of the composition. A non-limiting example of a volatile solvent is ethanol.

The aerosolized composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof. "Nonvolatile" refers to those materials that are liquid under ambient conditions and which have a measurable vapor pressure at 25° C. These materials typically have a vapor pressure less than about 0.01 mmHg, and an average boiling point typically greater than about 250° C. The aerosolized composition may also include one or more fragrances. Generally, the fragrance(s) may be present at a level from about 0.01% to about 40%, from about 0.1% to about 25%, from about 0.25% to about 20%, or from about 0.5% to about 15%, by weight of the composition. The compositions described herein may include water. If present, the water may comprise from about 0.1% to about 40%, from about 1% to about 30%, or from about 5% to about 20%, by weight, of the composition. In some examples, the aerosolized composition may includes a propellant; non-limiting examples include gaseous hydrocarbons and compressed air. In some examples, the aerosolized composition is aerosolized by the inherent design of the dispenser, such as by the use of a swirl chamber. The aerosolized composition may also include other ingredients; non-limiting examples of which include an antiperspirant active (for use in a body spray) or other materials like colorants (for use in a fine-fragrance).

In some examples, the multiple populations of microcapsules may be stored in a dispenser such that a first composition is stored in a first reservoir and a second composition stored in a second reservoir. The second composition may include a volatile solvent and a first fragrance. The first composition may include the multiple populations of microcapsules and a carrier (e.g. water). The first composition may further include a suspending agent. The first and second compositions may each further include any other ingredient listed herein unless such an ingredient negatively affects the performance of the microcapsules. Non-limiting examples of other ingredients include a coloring agent included in at least one of the first and second compositions and at least one non-encapsulated perfume oil in the second composition. When the first composition comprises microcapsules encapsulating a perfume oil, the first composition may further include a non-encapsulated perfume oil that may or may not differ from the encapsulated perfume oils in chemical make-up. In some examples, the first composition may be substantially free of a material selected from the group consisting of a propellant, ethanol, a detersive surfactant, and combinations thereof; preferably free of a material selected from the group consisting of a propellant, ethanol, a detersive surfactant, and combinations thereof. Non-limiting examples of propellants include compressed air, nitrogen, inert gases, carbon dioxide, gaseous hydrocarbons like propane, n-butane, isobutene, cyclopropane, and mixtures thereof. In some examples, the second composition may be substantially free of a material selected from the group consisting of a propellant, microcapsules, a detersive surfactant, and combinations thereof; preferably free of a material selected from the group consisting of propellant, microcapsules, a detersive surfactant, and combinations thereof.

Antiperspirant/Deodorant

The personal care composition may be an antiperspirant composition/deodorant. The personal care composition may include an antiperspirant active suitable for application to human skin. The concentration of the antiperspirant active in the antiperspirant composition should be sufficient to provide the desired enhanced wetness protection. For example, the active may be present in an amount of from about 0.1%, about 0.5%, about 1%, or about 5%; to about 60%, about 35%, about 25% or about 20%, by weight of the antiperspirant composition. These weight percentages are calculated on an anhydrous metal salt basis exclusive of water and any complexing agents such as glycine, glycine salts, or other complexing agents. Personal care compositions may also include a structurant to help provide the personal care composition with the desired viscosity, rheology, texture and/or product hardness, or to otherwise help suspend any dispersed solids or liquids within the personal care composition. The term "structurant" may include any material known or otherwise effective in providing suspending, gelling, viscosifying, solidifying, or thickening properties to the personal care composition or which otherwise provide structure to the final product form. Non-limiting examples of structurants include, for example, gelling agents, polymeric or nonpolymeric agents, inorganic thickening agents, or viscosifying agents. The concentration and type of the structurant selected for use in the personal care composition may vary depending upon the desired product form, viscosity, and hardness. The personal care compositions may include a surfactant. A surfactant is generally present at a level of about 0.05% to about 5%, by weight of the personal care composition, but may contain, from about 0.5% to about 5.0%; from about 1.0% to about 4%; from about 1.5% to about 3.5%; from about 1.75% to about 2.5%; about 2%, or any combination thereof. Personal care compositions may also include anhydrous liquid carriers. The anhydrous liquid carrier may be present, for example, at concentrations ranging from about 10%, about 15%, about 20%, about 25%; to about 99%, about 70%, about 60%, or about 50%, by weight of the personal care composition. Such concentrations will vary depending upon variables such as product form, desired product hardness, and selection of other ingredients in the personal care composition. The anhydrous carrier may be any anhydrous carrier known for use in personal care compositions or otherwise suitable for topical application to the skin. For example, anhydrous carriers may include, but are not limited to, volatile and nonvolatile fluids. The personal care composition may also include a malodor reducing agent.

Malodor reducing agents include components other than the antiperspirant active within the personal care composition that act to eliminate the effect that body odor has on fragrance display. These agents may combine with the offensive body odor so that they are not detectable including and may suppress the evaporation of malodor from the body, absorb sweat or malodor, mask the malodor, and/or prevent/ inhibit microbiological activity from odor causing organisms. The concentration of the malodor reducing agent within the personal care composition should be sufficient to provide such chemical or biological means for reducing or eliminating body odor. Although the concentration will vary depending on the agent used, generally, the malodor reducing agent may be included within the personal care composition from about 0.05%, about 0.5%, or about 1%; to about 15%, about 10%, or about 6%, by weight of the personal care composition. Malodor reducing agents may include, but are not limited to, pantothenic acid and its derivatives, petrolatum, menthyl acetate, uncomplexed cyclodextrins and derivatives thereof, talc, silica and mixtures thereof. Such agents may be used as described in U.S. Pat. No. 6,495,149, issued to Scavone, et al and US patent application 2003/0152539, filed Jan. 25, 2002 in the names of Scavone, et al.

The personal care compositions described herein may include a moisture-triggered fragrance technology delivery system that utilizes cyclic oligosaccharides, starches, starch-derivatives, polysaccharide-based encapsulation systems, and combinations thereof. As used herein, the term "cyclic oligosaccharide" means a cyclic structure comprising six or more saccharide units. The cyclic oligosaccharides may have six, seven, or eight saccharide units or mixtures thereof. It is common in the art to refer to six, seven and eight membered cyclic oligosaccharides as α, β, and γ, respectively. The cyclic oligosaccharides that may be useful include those that are soluble iii water, ethanol, or both water and ethanol. The cyclic oligosaccharides useful herein may have a solubility of at least about 0.1.21100 ml, at 25° C. and 1 atm of pressure in either water, ethanol, or both water and ethanol. The personal care compositions disclosed herein may comprise from about 0.001% to about 40%, from about 0.1% to about 25%, from about 0.3% to about 20%, from about 0.5% to about 10%, or from about 0.75% to about 5%, by weight of the personal care composition, of a cyclic oligosaccharide. The personal care compositions disclosed herein may comprise from 0.001% to 40%, from 0.1% to 25%, from 0.3% to 20%, from 0.5% to 10%, or from 0.75% to 5%, by weight of the personal care composition, of a cyclic oligosaccharide.

The personal care compositions may include one or more fragrances. As used herein, "fragrance" is used to indicate any odoriferous material. Any fragrance that is cosmetically acceptable may be used in the personal care composition. For example, the fragrance may be one that is a liquid at room temperature. Generally, the fragrance(s) may be present at a level from about 0.01% to about 40%, from about 0.1% to about 25%, from about 0.25% to about 20%, or from about 0.5% to about 15%, by weight of the personal care composition. The personal care compositions may also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

Cosmetic Composition

The personal care composition may take the form of a cosmetic composition that may be applied to mammalian keratinous tissue, including human skin. The cosmetic compositions may take various forms. For example, some non-limiting examples of forms include solutions, suspensions, lotions, creams, gels, toners, sticks, pencils, ointments, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

For example, the cosmetic composition may comprise from about 1% to about 95% by weight of water. The cosmetic composition may comprise from about 1% to about 95% by weight of one or more oils. Oils may be used to solubilize, disperse, or carry materials that are not suitable for water or water soluble solvents. Suitable oils include silicones, hydrocarbons, esters, amides, ethers, and mixtures thereof. When the cosmetic composition is in the form of an emulsion, oils are carriers typically associated with the oil phase. The cosmetic composition may be in the form of a water-in-oil emulsion, an oil-in-water emulsion, or a water-in-silicone emulsion such that the cosmetic composition may include water, a silicone, oil, and combinations thereof. The cosmetic compositions may include an emulsifier. An emulsifier is particularly suitable when the cosmetic composition is in the form of an emulsion or if immiscible materials are being combined. The cosmetic composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic, zwitterionic, or cationic. Non-limiting examples of emulsifiers are disclosed in U.S. Pat. Nos. 3,755,560, 4,421,769, and McCutcheon's, Emulsifiers and Detergents, 2010 Annual Ed., published by M. C. Publishing Co. Structuring agents may be used to increase viscosity, thicken, solidify, or provide solid or crystalline structure to the cosmetic composition. Structuring agents are typically grouped based on solubility, dispersibility, and phase compatibility. Examples of aqueous or water structuring agents include, but are not limited to, polymeric agents, natural or synthetic gums, polysaccharides, and the like. The cosmetic compositions may comprise from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the cosmetic composition, of one or more structuring agents. The cosmetic compositions may optionally contain one or more UV actives. As used herein, "UV active" includes both sunscreen agents and physical sunblocks. Suitable UV actives may be organic or inorganic. Examples of some suitable UV actives are listed in the functional category of "Sunscreen Agents" in the Personal Care Product Council's *International Cosmetic Ingredient Dictionary and Handbook*, Thirteenth Edition, 2010. The cosmetic compositions may be generally prepared by conventional methods such as those known in the art of making cosmetic compositions. Such methods typically involve mixing of ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The cosmetic compositions are preferably prepared such as to optimize stability (physical stability, chemical stability, photostability, etc.) and/or delivery of active materials. The cosmetic composition may be provided in a package sized to store a sufficient amount of the cosmetic composition for a treatment period. The size, shape, and design of the package may vary widely. Certain package examples are described in U.S. Pat. Nos. D570,707; D391, 162; D516,436; D535,191; D542,660; D547,193; D547,661; D558,591; D563,221; 2009/0017080; 2007/0205226; and 2007/0040306.

The cosmetic compositions disclosed herein may be applied to one or more skin surfaces and/or one or more mammalian keratinous tissue surfaces as part of a user's daily routine or regimen. Additionally or alternatively, the cosmetic compositions herein may be used on an "as needed" basis. In some examples, an effective amount of the cosmetic composition may be applied to the target portion of the keratinous tissue or skin. In some examples, the cosmetic composition may be provided in a package with written instructions detailing the application regimen.

Fabric and Home Care Compositions

In some examples, the consumer product may include a fabric and home care composition. In some examples, the fabric and home care composition may include from about 0.01% to about 20%, by weight of the composition, of microcapsules. As used herein, the term "fabric and home care compositions" include, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which are applicable may be in standard, concentrated or even highly concentrated form even to the extent that such products may in certain aspect be non-aqueous. Compositions may also be in the form of a unit dose and may be in the form of a single unit dose or a multi-compartment unit dose.

Adjunct Materials

The fabric and home care compositions may include adjunct ingredients non-limiting examples of which include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments, and combinations thereof. Other embodiments may not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. The precise nature of these additional components, and levels of incorporation thereof, will depend on the physical form of the composition and the nature of the operation for which it is to be used. However, when one or more adjunct materials are present, such one or more adjunct materials may be present as detailed below. The following is a non-limiting list of suitable adjunct materials.

Deposition Aid—In some examples, the fabric and home care composition may comprise from about 0.01% to about 10%, from about 0.05 to about 5%, or from about 0.15 to about 3%, by weight of the composition, of a deposition aid. In some examples, the deposition aid may be a cationic or amphoteric polymer. In some examples, the cationic polymer may have a cationic charge density of from about 0.005 to about 23 meq/g, from about 0.01 to about 12 meq/g, or from about 0.1 to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

In some examples, the deposition aid may comprise a cationic acrylic based polymer. In a further aspect, the deposition aid may comprise a cationic polyacrylamide. In another aspect, the deposition aid may comprise a polymer comprising polyacrylamide and polymethacrylamidopropyl trimethylammonium cation. In another aspect, the deposition aid may comprise poly(acrylamide-N-dimethyl aminoethyl acrylate) and its quaternized derivatives.

In some examples, the deposition aid may be selected from the group consisting of cationic or amphoteric polysaccharides. In some examples, the deposition aid may be selected from the group consisting of cationic and amphoteric cellulose ethers, cationic or amphoteric galactomannan, cationic guar gum, cationic or amphoteric starch, and combinations thereof.

Another group of suitable cationic polymers may include alkylamine-epichlorohydrin polymers which are reaction products of amines and oligoamines with epichlorohydrin. Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. In some examples, the MW of the cationic polymer may be from about 500 Daltons to about 37,500 Daltons.

Surfactants: Surfactants utilized may be of the anionic, nonionic, zwitterionic, ampholytic or cationic type or may comprise compatible mixtures of these types. Anionic and nonionic surfactants are typically employed if the composition is a laundry detergent. In contrast, cationic surfactants are typically employed if the composition is a fabric softener. In addition to the anionic surfactant, the compositions may further contain a nonionic surfactant. The compositions may contain up to from 0.01% to about 30%, alternatively from about 0.01% to about 20%, more alternatively from about 0.1% to about 10%, by weight of the composition, of a nonionic surfactant. In some examples, the nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

The fabric and home care compositions may contain up to about 30%, alternatively from about 0.01% to about 20%, more alternatively from about 0.1% to about 20%, by weight of the composition, of a cationic surfactant. Cationic surfactants include those which can deliver fabric care benefits, non-limiting examples which include: fatty amines; quaternary ammonium surfactants; and imidazoline quat materials.

Non-limiting examples of fabric softening actives are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate; 1, 2 di(stearoyloxy) 3 trimethyl ammoniumpropane chloride; dialkylenedimethylammonium salts such as dicanoladimethylammonium chloride, di(hard)tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N''-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of softener actives disclosed above are suitable for use herein.

Builders—The compositions may also contain from about 0.1% to 80% by weight of the composition of a builder. Compositions in liquid form generally contain from about 1% to 10% by weight of the composition of the builder component. Compositions in granular form generally contain from about 1% to 50% by weight of the composition of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites.

Dispersants—The compositions may contain from about 0.1%, to about 10%, by weight of the composition of dispersants. Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5% by weight of the composition. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3%, by weight of the composition, of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners—The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Other bleaching agents include metal complexes of transitional metals with ligands of defined stability constants.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In some examples, the organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

In some examples, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In some examples, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In some examples, the functionalized siloxane polymer may comprise an aminosilicone.

In some examples, the organosilicone may comprise amine ABn silicones and quat ABn silicones. Such organosilicones are generally produced by reacting a diamine with an epoxide.

In some examples, the functionalized siloxane polymer may comprise silicone-urethanes. These are commercially available from Wacker Silicones under the trade name SLM-21200®.

Perfume: The optional perfume component may comprise a component selected from the group consisting of
(1) a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;
(2) a pro-perfume;
(3) a low odor detection threshold perfume ingredients, wherein said low odor detection threshold perfume ingredients may comprise less than about 25%, by weight of the total neat perfume composition; and
(4) mixtures thereof; and Porous Carrier Microcapsule—A portion of the perfume composition can also be absorbed onto and/or into a porous carrier, such as zeolites or clays, to form perfume porous carrier microcapsules in order to reduce the amount of free perfume in the multiple use fabric conditioning composition.

Pro-perfume—The perfume composition may additionally include a pro-perfume. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen.

Fabric Hueing Agents—The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof. Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes U.S. Pat. No. 8,268,016 B2, or dyes as disclosed in U.S. Pat. No. 7,208,459 B2, and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In some examples, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In some examples, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenylmethane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

The hueing agent may be incorporated into the composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phtalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

The aforementioned fabric hueing agents can be used in combination (any mixture of fabric hueing agents can be used).

Structurants—Useful structurant materials that may be added to adequately suspend the benefit agent containing delivery particles include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey, U.S.A.

Anti-agglomeration agents—Useful anti-agglomeration agent materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

Coatings—In some examples, the microcapsules are manufactured and are subsequently coated with an additional material. Non-limiting examples of coating materials include but are not limited to materials selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey U.S.A.

Formaldehyde scavenger—In some examples, the microcapsules may be combined with a formaldehyde scavenger. Suitable formaldehyde scavengers include materials selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly (l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or Poly- Sciences, Inc. of Warrington, Pa., U.S.A. Such formaldehyde scavengers are typically combined with a slurry containing said benefit agent containing delivery particle, at a level, based on total slurry weight, of from about 2 wt. % to about 18 wt. %, from about 3.5 wt. % to about 14 wt. % or even from about 5 wt. % to about 13 wt. %.

In some examples, such formaldehyde scavengers may be combined with a product containing microcapsules, said scavengers being combined with said product at a level, based on total product weight, of from about 0.005% to about 0.8%, alternatively from about 0.03% to about 0.5%, alternatively from about 0.065% to about 0.25% of the product formulation.

In some examples, such formaldehyde scavengers may be combined with a slurry containing said benefit agent containing delivery particle, at a level, based on total slurry weight, of from about 2 wt. % to about 14 wt. %, from about 3.5 wt. % to about 14 wt. % or even from about 5 wt. % to about 14 wt. % and said slurry may be added to a product matrix to which addition an identical or different scavenger may be added at a level, based on total product weight, of from about 0.005% to about 0.5%, alternatively from about 0.01% to about 0.25%, alternatively from about 0.05% to about 0.15% of the product formulation, In some examples, one or more of the aforementioned formaldehyde scavengers may be combined with a liquid fabric enhancing product containing a benefit agent containing delivery particle at a level, based on total liquid fabric enhancing product weight, of from 0.005% to about 0.8%, alternatively from about 0.03% to about 0.4%, alternatively from about 0.06% to about 0.25% of the product formulation In some examples, such formaldehyde scavengers may be combined with a consumer product, for example, a liquid laundry detergent product containing microcapsules, said scavengers being selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid and mixtures thereof, and combined with said liquid laundry detergent product at a level, based on total liquid laundry detergent product weight, of from about 0.003 wt. % to about 0.20 wt. %, from about 0.03 wt. % to about 0.20 wt. % or even from about 0.06 wt. % to about 0.14 wt. %.

In some examples, such formaldehyde scavengers may be combined with a hair conditioning product containing microcapsules, at a level, based on total hair conditioning product weight, of from about 0.003 wt. % to about 0.30 wt. %, from about 0.03 wt. % to about 0.20 wt. % or even from about 0.06 wt. % to about 0.14 wt. %, said selection of scavengers being identical to the list of scavengers in the previous paragraph relating to a liquid laundry detergent product.

Test Methods

It is understood that the test methods that are disclosed in the Test Methods Section of the present application should be used to determine the respective values of the parameters of Applicants' invention as such invention is described and claimed herein.

(1) Fracture Strength a.) Place 1 gram of particles in 1 liter of distilled deionized (DI) water.

b.) Permit the particles to remain in the DI water for 10 minutes and then recover the particles by filtration.

c.) Determine the average rupture force of the particles by averaging the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the average fracture strength by dividing the average rupture force (in Newtons) by the average cross-sectional area of the spherical particle ($\pi r^2$, where r is the radius of the particle before compression), said average cross-sectional area being determined as follows:

(i) Place 1 gram of particles in 1 liter of distilled deionized (DI) water.

(ii) Permit the particles to remain in the DI water for 10 minutes and then recover the particles by filtration.

(iii) Determine the particle size distribution of the particle sample by measuring the particle size of 50 individual particles using the experimental apparatus and method of Zhang, Z.; Sun, G; "Mechanical Properties of Melamine-Formaldehyde microcapsules," J. Microencapsulation, vol 18, no. 5, pages 593-602, 2001.

(iv) Average the 50 independent particle diameter measurements to obtain an o average particle diameter.

d) For a capsule slurry, the sample is divided into three particle size fractions covering the particle size distribution. Per particle size fraction about 30 fracture strengths are determined.

(2) ClogP

"logP" is the octanol water partitioning coefficient and "ClogP" is the calculated logP computed by the Consensus algorithm implemented in ACD/Percepta version 14.02 by Advanced Chemistry Development, Inc. (ACD/Labs, Toronto, Canada).

(3) Boiling Point

Boiling point is measured by ASTM method D2887-04a, "Standard Test Method for Boiling Range Distribution of Petroleum Fractions by Gas Chromatography," ASTM International.

(4) Volume Weight Fractions

Volume weight fractions are determined via the method of single-particle optical sensing (SPOS), also called optical particle counting (OPC). Volume weight fractions are determined via an AccuSizer 780/AD supplied by Particle Sizing Systems of Santa Barbara Calif., U.S.A. or equivalent.

Procedure:

1) Put the sensor in a cold state by flushing water through the sensor;

2) Confirm background counts are less than 100 (if more than 100, continue the flush)

3) Prepare particle standard: pipette approx. 1 ml of shaken particles into a blender filled with approx. 2 cups of DI water. Blend it. Pipette approx. 1 ml of diluted, blended particles into 50 ml of DI water.
4) Measure particle standard: pipette approx. 1 ml of double diluted standard into Accusizer bulb. Press the start measurement-Autodilution button. Confirm particles counts are more than 9200 by looking in the status bar. If counts are less than 9200, press stop and 10 inject more sample.
5) Immediately after measurement, inject one full pipette of soap (5% Micro 90) into bulb and press the Start Automatic Flush Cycles button.

(5) Volume Weighted Fracture Strength (VWFS)

$$VWFS = (\text{fracture strength}_1 \times \text{volume fraction}_1) + (\text{fracture strength}_2 \times \text{volume fraction}_2) + (\text{fracture strength}_3 \times \text{volume fraction}_3)$$

Fracture strength$_1$=average fracture strength measured from a pool of 10 microcapsules (with similar particle size)
Volume fraction$_1$=volume fraction determined via Accusizer of particle distribution corresponding to fracture strength$_1$
The spread around the fracture strength to determine the volume fraction is determined as follows:
For particle batches with a mean particle sizes of about 15 micrometers a spread of about 10 micrometers is used, for particle batches with a mean particle sizes of about 30 micrometers and above, a spread of about 10 to 15 micrometers is used.

| Particle Batch | Mean Particle Size | Fracture Strength Determination at 3 particle sizes | Volume Fractions | Volume Fracture Strength |
|---|---|---|---|---|
| Melamine-based polyurea | 31 microns | 21 micron, 1.8 MPa; 31 micron, 1.6 MPa; 41 micron, 1.2 MPa) | 1 to 25 microns, 30%; 25 to 36 microns, 40%; 36 to 50 microns, 30% | 1.5 MPa |

(6) Benefit Agent Leakage Test
a.) Obtain 2, one gram samples of benefit agent particle composition.
b.) Add 1 gram (Sample 1) of particle composition to 99 grams of product matrix that the particle will be employed in and with the second sample immediately proceed to Step d below.
c.) Age the particle containing product matrix (Sample 1) of a.) above for 2 weeks at 35° C. in a sealed, glass jar.
d.) Recover the particle composition's particles from the product matrix of c.)
(Sample 1 in product matrix) and from particle composition (Sample 2) above by filtration.
e.) Treat each particle sample from d.) above with a solvent that will extract all the benefit agent from each samples' particles.
f.) Inject the benefit agent containing solvent from each sample from e.) above into a Gas Chromatograph and integrate the peak areas to determine the total quantity of benefit agent extracted from each sample.
g.) The benefit agent leakage is defined as:
Value from f.) above for Sample 2–Value from f.) above for Sample 1.

(7) Test Method for Determining Median Volume-Weighted Particle Size of Microcapsules
One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in deionized water to form a capsule slurry for characterization for particle size distribution.
The median volume-weighted particle size of the microcapsules is measured using an Accusizer 780A, made by Particle Sizing Systems, Santa Barbara Calif., or equivalent. The instrument is calibrated from 0 to 300 µm using particle size standards (as available from Duke/Thermo-Fisher-Scientific Inc., Waltham, Mass., USA). Samples for particle size evaluation are prepared by diluting about 1 g of capsule slurry in about 5 g of de-ionized water and further diluting about 1 g of this solution in about 25 g of water. About 1 g of the most dilute sample is added to the Accusizer and the testing initiated using the autodilution feature. The Accusizer should be reading in excess of 9200 counts/second. If the counts are less than 9200 additional sample should be added. Dilute the test sample until 9200 counts/second and then the evaluation should be initiated. After 2 minutes of testing the Accusizer will display the results, including the median volume-weighted particle size.

(8) Olfactive Analysis of Leave-on-Treatment Product
a.) 0.40 milliliters of Leave-on-Conditioner product is applied to a hair switch (IHI, 4 grams, 8 inches long, moderately damaged grade) that has been combed, wet, and lightly squeeged. Lather switch 50-60 strokes (30 seconds) in a milking action.
b.) Leave hair to dry at ambient temperature by hanging it on a rack. After approximately 3 hours, olfactively grade the hair switch according to the Primavera Grade (0-100 scale for intensity, where a 10 point difference is consumer noticeable). Record this as the Initial Pre-Comb fragrance intensity.
c.) Comb the hair switch 3 times and olfactively grade, record this as the Initial Post-Comb fragrance intensity.
d.) Leave the hair switch under ambient conditions (70 degrees Fahrenheit and 30% relative humidity) for 24 hours. Then, olfactively grade the hair switch according to the Primavera Grade (0-100 scale for intensity, where a 10 point difference is consumer noticeable), record this as the 24 hr aged Pre-Comb olfactive intensity. Comb the hair switch 3 times and assign an olfactive grade, record this as the 24 hr aged Post-Comb olfactive intensity.

(9) Olfactive Analysis of Shampoo Product
a. 0.4 milliliters of Shampoo product is applied to a hair switch (IHI, 4 grams, 8 inches long, moderately damaged grade) that has been combed, wet, and lightly squeeged. Lather switch 50-60 strokes (30 seconds) in a milking action.
b. Rinse with stationary shower rinse with no manipulation of hair (100 degrees Fahrenheit water temperature, water flow at 1.5 gallons per minute, for 30 seconds, water hardness of 8 grains per gallon). Lightly squeegee once down the hair switch from top to bottom between fingers after rinsing to remove excess water.
c. Repeat application of product per step (a), milking, rinsing, and squeeging per step (b).
d. Leave hair to dry at ambient temperature by hanging it on a rack. After approximately 3 hours, olfactively grade the hair switch according to the Primavera Grade (0-100 scale for intensity, where a 10 point difference is consumer noticeable). Record this as the Initial Pre-Comb fragrance intensity.
e. Comb the hair switch 3 times and olfactively grade, record this as the Initial Post-Comb fragrance intensity.
f. Leave the hair switch under ambient conditions (70 degrees Fahrenheit and 30% relative humidity) for 24 hours. Then, olfactively grade the hair switch according to the Primavera Grade (0-100 scale for intensity, where a 10 point difference is consumer noticeable), record this as the 24 hr aged Pre-Comb olfactive intensity. Comb the hair switch 3 times and assign an olfactive grade, record this as the 24 hr aged Post-Comb olfactive intensity.

EXAMPLES

The following examples illustrate the present invention. The exemplified compositions may be prepared by conventional formulation and mixing techniques. It will be appreciated that other modifications of the present invention within the skill of those in the art may be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of microcapsules and compositions described herein.

A perfume composition, called Scent A, is utilized to prepare the examples of the invention. The table below lists the ingredients of Scent A. Table 5 provides the ClogP breakdown of the perfume oil encapsulated.

TABLE 5

| Perfume Material | Clog P |
|---|---|
| 3,6-Nonadien-1-ol | 2.523 |
| Allyl Caproate | 3.355 |
| Allyl Heptoate | 3.706 |
| Beta Gamma Hexenol | 1.425 |
| Cis 3 Hexenyl Acetate | 2.189 |
| Cis-6-Nonen-1-OL FCC | 2.518 |
| Cyclo Galbanate | 2.883 |
| Cymal | 3.607 |
| Dihydro Myrcenol | 3.088 |
| Dimethyl Benzyl Carbinyl Butyrate | 4.047 |
| Ethyl 2 Methyl Pentanoate | 2.47 |
| Ethyl Acetoacetate | 0.385 |
| Ethyl Caproate FCC | 2.832 |
| Ethyl Maltol | 0.504 |
| Ethyl Oenanthate | 3.148 |
| Ethyl-2-Methyl Butyrate | 1.985 |
| Florhydral | 3.607 |
| Hexamethylindanopyran | 5.933 |
| Gamma Decalactone | 2.709 |
| Hexyl Acetate | 2.827 |
| Ionone Beta | 3.824 |
| Jasmolactone | 1.788 |
| Liffarome | 1.824 |
| Ligustral Or Triplal | 2.984 |
| Linalool | 3.285 |
| Melonal | 3.136 |
| Nectaryl | 4.202 |
| Para Hydroxy Phenyl Butanone | 1.425 |
| Pino Acetaldehyde | 3.761 |
| Prenyl Acetate | 1.894 |
| Thesaron | 4.382 |
| Undecalactone | 3.179 |
| Undecavertol | 3.973 |
| Verdox | 4.46 |
| Verdural B Extra | 2.955 |

Example 1: 90 wt % Core/10 wt % Wall, Scent A Capsules, 20% Partitioning Modifier An oil solution, consisting of 128.4 g of perfume Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This mixture is hereafter referred to as oil solution A.

In a reactor vessel, an aqueous solution is prepared consisting of 300 g of deionized water to which is dispersed in 2.40 grams of Celvol 540 polyvinyl alcohol at 25° C. The mixture is heated to 85° C. and held there for 45 minutes. The solution is cooled to 30° C. 1.03 grams of Wako Chemicals V-501 initiator is added, along with 0.51 grams of a 40% sodium hydroxide solution. The solution is then heated to 50° C., and the solution is maintained at that temperature.

To oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This mixture is hereafter referred to as oil solution B. Use a Caframo mixer with a 4-blade pitched turbine agitator to achieve the desired oil-in-water emulsion particle size.

Start a nitrogen blanket on top of the aqueous solution in reactor. Start transferring oil solution B into the aqueous solution in the reactor with minimal mixing. Increase the agitation of mixing to 1800-2500 rpm for a period of 60 minutes to emulsify the oil phase into the water solution. After milling is completed, mixing is continued with a 3" propeller at 350 rpm. The batch is then held at 50° C. for 45 minutes. The temperature is then increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 12.6 microns, a fracture strength of 7.68±2.0 MPa, and a deformation at fracture of 51%±20%.

Example 2. 90 wt % Core/10 wt % Wall, Scent A Capsules, 40% Partitioning Modifier An oil solution, consisting of 96 g Perfume oil Oil, 64 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This mixture is hereafter referred to as oil solution A.

In a reactor vessel, an aqueous solution is prepared consisting of 300 g of deionized water to which is dispersed in 2.40 grams of Celvol 540 polyvinyl alcohol at 25° C. The mixture is heated to 85° C. and held there for 45 minutes. The solution is cooled to 30° C. 1.03 grams of Wako Chemicals V-501 initiator is added, along with 0.51 grams of a 40% sodium hydroxide solution. The solution is then heated to 50° C., and the solution is maintained at that temperature.

To oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This mixture is hereafter referred to as oil solution B. Use a Caframo mixer with a 4-blade pitched turbine agitator to achieve the desired oil-in-water emulsion particle size.

Start a nitrogen blanket on top of the aqueous solution in reactor. Start transferring oil solution B into the aqueous solution in the reactor with minimal mixing. Increase the agitation of mixing to 1800-2500 rpm for a period of 60 minutes to emulsify the oil phase into the water solution. After milling is completed, mixing is continued with a 3" propeller at 350 rpm. The batch is then held at 50° C. for 45 minutes. The temperature is then increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 12.6 microns, a fracture strength of 2.60±1.2 MPa, 37%±15% deformation at fracture.

Example 3: 90 wt % Core/10 wt % Wall, Scent A Capsules, 20% Partitioning Modifier An oil solution, consisting of 128.4 g Perfume oil Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g of deionized water to which is dispersed in 2.40 grams of Celvol 540 polyvinyl alcohol at 25° C. The mixture is heated to 85° C. and held there for 45 minutes. The solution is cooled to 30° C. 1.03 grams of Wako Chemicals V-501 initiator is added, along with 0.51 grams of a 40% sodium hydroxide solution. The solution is then heated to 50° C., and the solution is maintained at that temperature.

To oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This mixture is hereafter referred to as oil solution B. Use a Caframo mixer with a 4-blade pitched turbine agitator to achieve the desired oil-in-water emulsion particle size.

Start a nitrogen blanket on top of the aqueous solution in reactor. Start transferring oil solution B into the aqueous solution in the reactor with minimal mixing. Increase the agitation of mixing to 1800-2500 rpm for a period of 60 minutes to emulsify the oil phase into the water solution. After milling is completed, mixing is continued with a 3" propeller at 350 rpm. The batch is then held at 50° C. for 45 minutes. The temperature is then increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 26.1 microns, a fracture strength of 1.94±1.2 MPa, 30%±14% deformation at fracture.

Example 4: 90 wt % Core/10 wt % Wall, Scent A Capsules, 20% Partitioning Modifier An oil solution, consisting of 128.4 g Perfume oil Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g of deionized water to which is dispersed in 2.40 grams of Celvol 540 polyvinyl alcohol at 25° C. The mixture is heated to 85° C. and held there for 45 minutes. The solution is cooled to 30° C. 1.03 grams of Wako Chemicals V-501 initiator is added, along with 0.51 grams of a 40% sodium hydroxide solution. The solution is then heated to 50° C., and the solution is maintained at that temperature.

To oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This mixture is hereafter referred to as oil solution B. Use a Caframo mixer with a 4-blade pitched turbine agitator to achieve the desired oil-in-water emulsion particle size.

Start a nitrogen blanket on top of the aqueous solution in reactor. Start transferring oil solution B into the aqueous solution in the reactor with minimal mixing. Increase the agitation of mixing to 1800-2500 rpm for a period of 60 minutes to emulsify the oil phase into the water solution. After milling is completed, mixing is continued with a 3" propeller at 350 rpm. The batch is then held at 50° C. for 45 minutes. The temperature is then increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 10.0 microns, a fracture strength of 7.64±2.2 MPa, 56%±20% deformation at fracture.

Examples 5-8. Leave-on Conditioner Formulations Containing Microcapsules

The microcapsules of Examples 1-4 are formulated into a leave-on conditioner matrix to deliver 0.30 wt % Scent A (equivalent to delivering 300 micrograms of perfume oil per gram of hair using the Olfactive Analysis of Leave-On Treatment Product Test Method) as described in Table 6 below.

TABLE 6

| Material | Example 5 (grams) | Example 6 (grams) | Example 7 (grams) | Example 8 (grams) |
|---|---|---|---|---|
| PREMIX | | | | |
| Water | 22.89 | 22.89 | 22.89 | 22.89 |
| Silicone | 0.57 | 0.57 | 0.57 | 0.57 |
| Cetyl, Stearyl, Oleyl alcohol | 0.59 | 0.59 | 0.59 | 0.59 |
| Behenyl Trimethylammonium chloride BTMAC | 0.21 | 0.21 | 0.21 | 0.21 |
| Stearamidopropyl Dimethylamine | 0.35 | 0.35 | 0.35 | 0.35 |
| Preservatives | 0.50 | 0.50 | 0.50 | 0.50 |
| EDTA | 0.22 | 0.22 | 0.22 | 0.22 |
| Panthenyl ethyl ether | 0.31 | 0.31 | 0.31 | 0.31 |
| Hydroxyethyl cellulose | 0.32 | 0.32 | 0.32 | 0.32 |

TABLE 6-continued

| Material | Example 5 (grams) | Example 6 (grams) | Example 7 (grams) | Example 8 (grams) |
|---|---|---|---|---|
| Polyethylene glycol PEG 2M | 0.28 | 0.28 | 0.28 | 0.28 |
| Quaternium-18 | 0.32 | 0.32 | 0.32 | 0.32 |
| Citric acid - anhydrous | 0.22 | 0.22 | 0.22 | 0.22 |
| POST-ADDS | | | | |
| PMCs of Example 1 | 0.29 | 0.00 | 0.00 | 0.00 |
| PMCs of Example 2 | 0.00 | 0.40 | 0.00 | 0.00 |
| PMCs of Example 3 | 0.00 | 0.00 | 0.30 | 0.00 |
| PMCs of Example 4 | 0.00 | 0.00 | 0.00 | 0.29 |
| Water | 0.21 | 0.10 | 0.20 | 0.21 |

Examples 9A-9E & 10. Conditioners

| Material | Example 9A (g) | Example 9B (g) | Example 9C (g) | Example 9D (g) | Example 9E (g) | Example 10 (g) |
|---|---|---|---|---|---|---|
| PREMIX | | | | | | |
| Water | 22.89 | 22.89 | 22.89 | 22.89 | 22.89 | 22.89 |
| Silicone | 0.57 | 0.57 | 0.57 | 0.57 | 0.57 | 0.57 |
| Cetyl, Stearyl, Oleyl alcohol | 0.59 | 0.59 | 0.59 | 0.59 | 0.59 | 0.59 |
| BTMAC | 0.21 | 0.21 | 0.21 | 0.21 | 0.21 | 0.21 |
| Stearamidopropyl Dimethylamine | 0.35 | 0.35 | 0.35 | 0.35 | 0.35 | 0.35 |
| Preservatives | 0.50 | 0.50 | 0.50 | 0.50 | 0.50 | 0.50 |
| EDTA | 0.22 | 0.22 | 0.22 | 0.22 | 0.22 | 0.22 |
| Panthenyl ethyl ether | 0.31 | 0.31 | 0.31 | 0.31 | 0.31 | 0.31 |
| Hydroxyethyl cellulose | 0.32 | 0.32 | 0.32 | 0.32 | 0.32 | 0.32 |
| PEG 2M | 0.28 | 0.28 | 0.28 | 0.28 | 0.28 | 0.28 |
| Quaternium-18 | 0.32 | 0.32 | 0.32 | 0.32 | 0.32 | 0.32 |
| Citric acid-anhydrous | 0.22 | 0.22 | 0.22 | 0.22 | 0.22 | 0.22 |
| POST-ADDS | | | | | | |
| PMCs of Example 1 | 0.392 | 0.00 | 0.35 | 0.25 | 0.18 | 0.25 |
| PMCs of Example 2 | 0.00 | 0.54 | 0.17 | 0.22 | 0.27 | 0.00 |
| PMCs of Example 3 | 0.00 | 0.00 | 0.00 | 0.00 | 0.00 | 0.22 |
| Water | 0.108 | 0.00 | 0.00 | 0.03 | 0.07 | 0.03 |

Example 11. Polyurea/Urethane Capsules

An aqueous solution, consisting of 6.06 g Celvol 523 polyvinyl alcohol (Celanese Chemicals) and 193.94 g deionized water, is added into a temperature controlled steel jacketed reactor at room temperature. Then an oil solution, consisting of 75 g Scent A and 25 g Desmodur N3400 (polymeric hexamethylene diisocyanate), is added into the reactor. The mixture is emulsified with a propeller (4 tip, 2" diameter, flat mill blade; 2200 rpm) to desired emulsion droplet size. The resulting emulsion is then mixed with a Z-bar propeller at 450 rpm. An aqueous solution, consisting of 47 g water and 2.68 g tetraethylenepentamine, is added into the emulsion. And it is then heated to 60° C., held at 60° C. for 8 hours, and allowed to cool to room temperature. The median particle size of the formed microcapsules is 10 microns.

Example 12. Polyurea/Urethane Capsules

Prepare the Oil Phase by adding 4.44 grams of isophorone diisocyanate (Sigma Aldrich) to 5.69 grams of Scent A perfume oil oil. Prepare a Water Phase by mixing 1.67 grams of Ethylene Diamine (Sigma Aldrich) and 0.04 grams of 1,4-Diazabicyclo[2.2.2]octane (Sigma Aldrich) into 40 grams of a 5 wt % aqueous solution of Polyvinylpyrrolidone K-90 (Sigma Aldrich) at 10 degrees Centigrade. Next, add the Oil Phase contents to 15.0 grams of a 5 wt % aqueous solution of Polyvinylpyrrolidone K-90 (Sigma Aldrich), while agitating the mix at 1400 RPM using a Janke & Kunkel IKA Laboretechnik RW20 DZM motor with a 3-blade turbine agitator for approximately 9 minutes. Next, add the addition of the Water Phase into the emulsified Oil Phase dropwise over a 6.5 minute period, while continuing to agitate at 1400 RPM. Continue to agitate for 23 minutes, then reduce the agitation speed to 1000 RPM. After 3.75 additional hours, reduce the agitation speed to 500 RPM, and continue to agitate for 14 hours. Start heating the dispersion to 50 degrees Centigrade, over a 2 hour period. Age the capsules at 50 C for 2 hours, then collect the formed microcapsules. The resulting polyurea/urethane particles have a median particle size of 12 microns.

Example 13. Polyurea/Urethane Capsules

The same procedure as outlined in Example 12 is followed, except that the Perfume oil Oil comprises 80 wt % Scent A and 20 wt % Isopropyl Myristate. The formed microcapsules have a median particle size of 11 microns.

Example 14. Polyurea/Urethane Capsules

The same procedure as outlined in Example 12 is followed, except that the Perfume oil Oil comprises 60 wt % Scent A and 40 wt % Isopropyl Myristate. The formed microcapsules have a median particle size of 11 microns.

Example 14B. Resorcin Capsules

In a 400 mL beaker, 5.5 g resorcin are dissolved in water while stirring (stirring speed: approximately 1,500 rpm) and then mixed with 2.0 g sodium carbonate solution (20 wt %), upon which the pH is 7.9. The solution is heated to a temperature of approximately 52° C. 25.5 g glutardialdehyde are then added. The mixture is stirred for approximately an additional 10 minutes at a stirring speed of approximately 1,500 rpm and a temperature of approximately 52° C. (pre-condensation time). Afterward, approximately 20 g water are added and approximately 2 minutes later, 1 g of one of the protective colloids (a) copolymer 1.1a, (b) copolymer 1.1b and (c) poly-AMPS (AMPS homopolymer) is added and approximately another 2 minutes later 45 g butyl phenylacetate (CAS No. 122-43-0; aromatic substance with a honey-like aroma) and 10 g isopropyl myristate (CAS No. 110-27-0; odorless diluent for aroma oils) are added Immediately afterward, the stirring speed is increased to approximately 4,000 rpm and at approximately the same time, 20.0 g sodium carbonate solution (20 wt %) are added. Afterward the pH of the mixture is approximately 9.7. Subsequently, the viscosity and the volume of the mixture increase. Stirring is continued at a stirring speed of approximately 4,000 rpm until the viscosity drops again. Only then is the stirring speed reduced to approximately 1,500 rpm. The preparation is stirred for an additional approximately 60 minutes at a temperature of approximately 52° C. and at a roughly constant stirring speed. This phase is also called the dwell phase. The mixture is then heated to approximately 80° C. and the capsules are hardened at this temperature for a period of 3 hours.

Capsule size distribution—D (90) 5 to 10 µm; encapsulation efficiency approx. 90%;

Drying yield >90%; solids of the slurry approximately 40 wt %.

The capsules produced are formaldehyde-free and can be processed without any problems from the aqueous slurry into a dry, free-flowing powder as stable core/shell microcapsules. The capsules can also be loaded with other gaseous, liquid or solid hydrophobic materials and substance classes instead of with butyl phenyl acetate, in particular with aromatic substances and/or perfume oils.

Example 15. Spray Drying of Perfume Microcapsules

The perfume microcapsule slurry of Example 1 to 4 is pumped at a rate of 1 kg/hr into a co-current spray dryer (Niro Production Minor, 1.2 meter diameter) and atomized using a centrifugal wheel (100 mm diameter) rotating at 18,000 RPM. Dryer operating conditions are: air flow of 80 kg/hr, an inlet air temperature of 200 degrees Centigrade, an outlet temperature of 100 degrees Centigrade, dryer operating at a pressure of −150 millimeters of water vacuum. The dried powder is collected at the bottom of a cyclone. The collected particles have an approximate particle diameter of 11 microns. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 16. Spray Drying of Perfume Microcapsules

The perfume microcapsule slurry of Example 1 to 4 is mixed with a 25 wt % aqueous solution of HICAP 100 (Ingredion) in a ratio of 2:1 slurry: starch aqueous solution, and is pumped at a rate of 1 kg/hr into a co-current spray dryer (Niro Production Minor, 1.2 meter diameter) and atomized using a centrifugal wheel (100 mm diameter) rotating at 18,000 RPM. Dryer operating conditions are: air flow of 80 kg/hr, an inlet air temperature of 200 degrees Centigrade, an outlet temperature of 100 degrees Centigrade, dryer operating at a pressure of −150 millimeters of water vacuum. The dried powder is collected at the bottom of a cyclone. The collected particles have an approximate particle diameter of 11 microns. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 17. Agglomeration of Encapsulates 800 g aliquots of perfume microcapsule slurry, of Examples 1 to 4, are each mixed together with 200 g of carboxymethyl cellulose (CP Kelco) using a spatula until a uniform paste has been formed. Thus four separate pastes are produced. Each paste is then passed through an APV 19 mm barrel twin screw extruder (Baker Perkins Ltd.) using conveying screws only and a die plate with 1 mm diameter holes. The extruder is run at a speed of 100 rpm and at ambient temperature to form three sets of extrudates. Following the extrusion operation, each set of extrudates are spread out as a thin layer onto separate trays and placed in an oven to dry at 50° C. until they reach a moisture content of 20 wt %. Each set of dried extrudates are then broken up by hand and sieved through a 2000 micron screen to remove the majority of the longer extrudates. The efficiency of the process may be improved via the addition of a dusting agent following the extrusion step to avoid coagulation during drying.

Example 18. Agglomeration of Encapsulates 1 kg aliquots of perfume microcapsule slurry, of Examples 1 to 4, are each mixed with 100 g of a cross-linked polyacrylate (Aqualic CA-Series, Nippon Shokubai) using a spatula until the mix forms a wet mass of discrete particles. Each set of wet particles is placed into separate plastic bags and dusted with 300 g of Zeolite 4A (Industrial Chemicals Ltd), until free flowing agglomerate particles are formed. 250 g aliquots of perfume microcapsule slurry, of Examples 1 to 3, are each mixed with 5 g of a cross-linked polyacrylate (Aqualic CA Series, Nippon Shokubai) using a spatula until the mix forms a paste. 100 g of each paste is separately mixed together with 50 g of Zeolite 4A (Industrial Chemicals Ltd) in a kitchen food processor (Braun) thus forming three sets of agglomerate particles. Following mixing, each set of agglomerate particles is screened using a 2000 micron sieve to remove the oversize. The good product passing through the screen for each agglomerate particle set is dried by spreading a thin layer of the material on a tray and placing in an oven at 50° C. until the agglomerate particles reach a moisture content of 20 wt %.

Example 19. Agglomeration of Encapsulates

Sodium alginate powder (Manucol D M, International Speciality Products) is dissolved in four separate aliquots of perfume microcapsule slurry from Examples 1 to 4 to form 1% alginate solutions. These compositions are mixed thoroughly using an Ultra Turrax T25 mixer (IKA) at a speed of 10000/min. The PMC/alginate mixtures are then added drop wise to separate 1% aqueous solutions of chitosan (Primex). The beads remain in the chitosan solution until they have cured, typically 10-45 minutes (cure time depends on grade and concentration of chitosan used). Following the curing step, the material is removed and dried at 37° C. to a moisture content of 12 wt % thus producing three separate sets of beads.

Example 20A-20J. Microcapsules in Shampoo

A subset of the microcapsules from the above examples is formulated into a rinse-off Shampoo formulation as follows: to 90.0 grams of shampoo formulation (with a typical formulation given below) is added an appropriate amount of microcapsule slurry of examples 1 through 2 to deliver a Scent A perfume oil usage level of 0.6 wt %. The microcapsules and water are added on top of the shampoo formulation, then the contents are mixed using a SpeedMixer by Hauschild DAC 400FVZ mixer, at 1850 RPM for 1 minute.

| Example | Level of partitioning modifier | % Scent A Perfume oil in Capsule Slurry | Quantity of Shampoo Product (g) | Quantity of Fragrance Delivery Technology (g) | Quantity of Water (g) |
|---|---|---|---|---|---|
| Neat Perfume | 0% | N/A | 90.00 | 0.60 | 9.40 |
| 1 | 20% | 25% | 90.00 | 2.40 | 7.60 |
| 2 | 40% | 20% | 90.00 | 3.00 | 7.00 |

Typical composition of shampoo formulations are given in the examples below.

| | EXAMPLE | | |
|---|---|---|---|
| Ingredient | 20A | 20B | 20C |
| Water | QS | QS | QS |
| Polyquaternium 76[1] | 2.50 | — | — |
| Guar, Hydroxylpropyl Trimonium Chloride[2] | — | 0.25 | — |
| Polyquaterium 6[3] | — | — | 0.79 |
| Sodium Laureth Sulfate (SLE3S)[4] | 21.43 | 21.43 | 21.43 |
| Sodium Lauryl Sulfate (SLS)[5] | 20.69 | 20.69 | 20.69 |
| Silicone[6] | 0.75 | 1.00 | 0.5 |
| Cocoamidopropyl Betaine[7] | 3.33 | 3.33 | 3.33 |
| Cocoamide MEA[8] | 1.0 | 1.0 | 1.0 |
| Ethylene Glycol Distearate[9] | 1.50 | 1.50 | 1.50 |
| Sodium Chloride[10] | 0.25 | 0.25 | 0.25 |
| Fragrance | 0.70 | 0.70 | 0.70 |
| Fragrance Microcapsule of Example 1 | 0.8 | 0.8 | 0.8 |
| Fragrance Microcapsules of Example 2 | 2.0 | 2.0 | 2.0 |
| Preservatives, pH adjustment | 1% | 1% | 1% |

[1]Mirapol AT-1, Copolymer of Acrylamide(AM) and TRIQUAT, MW = 1,000,000; CD = 1.6 meq./gram; 10% active; Supplier Rhodia
[2]Jaguar C500, MW - 500,000, CD = 0.7, supplier Rhodia
[3]Mirapol 100S, 31.5% active, supplier Rhodia
[4]Sodium Laureth Sulfate, 28% active, supplier: P&G
[5]Sodium Lauryl Sulfate, 29% active supplier: P&G
[6]Glycidol Silicone VC2231-193C
[7]Tegobetaine F-B, 30% active supplier: Goldschmidt Chemicals
[8]Monamid CMA, 85% active, supplier Goldschmidt Chemical
[9]Ethylene Glycol Distearate, EGDS Pure, supplier Goldschmidt Chemical
[10]Sodium Chloride USP (food grade), supplier Morton; note that salt is an adjustable ingredient, higher or lower levels may be added to achieve target viscosity.

| Ingredient | EXAMPLE | | |
|---|---|---|---|
| | 20D | 20E | 20F |
| Water | QS | QS | QS |
| Silicone A[1] | 1.0 | — | — |
| Silicone B[2] | — | 0.5 | — |
| Silicone C[3] | — | — | 0.5 |
| Cyclopentasiloxane[4] | — | 0.61 | 1.5 |
| Behenyl trimethyl ammonium chloride[5] | 2.25 | 2.25 | 2.25 |
| Isopropyl alcohol | 0.60 | 0.60 | 0.60 |
| Cetyl alcohol[6] | 1.86 | 1.86 | 1.86 |
| Stearyl alcohol[7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/ Methylisothiazolinone[8] | 0.0005 | 0.0005 | 0.0005 |
| Panthenol[9] | 0.10 | 0.10 | 0.10 |
| Panthenyl ethyl ether[10] | 0.05 | 0.05 | 0.05 |
| Fragrance | 0.35 | 0.35 | 0.35 |
| Fragrance Microcapsules (Example 1) | 0.8 | 0.8 | 0.8 |
| Fragrance Microcapsules of Example 2 | 2.0 | 2.0 | 2.0 |

[1]Glycidol Silicone VC2231-193
[2]Glycidol Silicone VC2231-193F
[3]Glycidol Silicone VC2231-193A
[4]Cyclopentasiloxane: SF1202 available from Momentive Performance Chemicals
[5]Behenyl trimethyl ammonium chloride/Isopropyl alcohol: Genamin ™ KMPavailable from Clariant
[6]Cetyl alcohol: Konol ™ series available from Shin Nihon Rika
[7]Stearyl alcohol: Konol ™ series available from Shin Nihon Rika
[8]Methylchloroisothiazolinone/Methylisothiazolinone: Kathon TM CG available from Rohm & Haas
[9]Panthenol: Available from Roche
[10]Panthenyl ethyl ether: Available from Roche

| Ingredient | EXAMPLE | | | |
|---|---|---|---|---|
| | 20G | 20H | 20I | 20J |
| Sodium Laureth Sulfate | 10.00 | 10.00 | 10.00 | 10.00 |
| Sodium Lauryl Sulfate | 1.50 | 1.50 | 1.50 | 1.50 |
| Cocamidopropyl betaine | 2.00 | 2.00 | 2.00 | 2.00 |
| Guar Hydroxypropyl trimonium chloride (1) | 0.40 | | 0.40 | |
| Guar Hydroxypropyl trimonium chloride (2) | | 0.40 | | 0.40 |
| Dimethicone (3) | 2.00 | 2.00 | 2.00 | 2.00 |
| Gel Network (4) | | 27.27 | | 27.27 |
| Ethylene Glycol Distearate | 1.50 | 1.50 | 1.50 | 1.50 |
| 5-Chloro-2-methyl-4-isothiazolin-3-one, Kathon CG | 0.0005 | 0.0005 | 0.0005 | 0.0005 |
| Sodium Benzoate | 0.25 | 0.25 | 0.25 | 0.25 |
| Disodium EDTA | 0.13 | 0.13 | 0.13 | 0.13 |
| Perfume | 0.70 | 0.70 | 0.70 | 0.70 |
| Fragrance Microcapsules of Example 1 | 0.8 | 0.8 | 1.2 | 1.2 |
| Fragrance Microcapsules of Example 2 | 2.0 | 2.0 | 1.5 | 1.5 |
| Citric Acid/Sodium Citrate Dihydrate | pH QS | pH QS | pH QS | pH QS |
| Sodium Chloride/Ammonium Xylene Sulfonate | Visc. QS | Visc. QS | Visc. QS | Visc. QS |
| Water | QS | QS | QS | QS |

(1) Jaguar C17 available from Rhodia (2) N-Hance 3269 (with Mol. W. of ~500,000 and 0.8 meq/g) available from Aqulaon/Hercules (3) Viscasil 330M available from General Electric Silicones (4) Gel Networks; See Composition below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

| Ingredient | Wt. % |
| --- | --- |
| Water | 86.14% |
| Cetyl Alcohol | 3.46% |
| Steary Alcohol | 6.44% |
| Sodium laureth-3 sulfate (28% Active) | 3.93% |
| 5-Chloro-2-methyl-4-isothiazolin-3-one, Kathon CG | 0.03% |

Example 21A-21C. Microcapsules in Lotion

For the examples above, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

| | Example | | |
| --- | --- | --- | --- |
| | 21A | 21B | 21C |
| PHASE A | | | |
| DC-9040[1] | 8.60 | 3.00 | 5.00 |
| Dimethicone | 4.09 | 4.00 | 4.00 |
| Polymethylsilsesquioxane[2] | 4.09 | 4.00 | 4.00 |
| Cyclomethicone | 11.43 | 0.50 | 11.33 |
| KSG-210[3] | 5.37 | 5.25 | 5.40 |
| Polyethylene wax[4] | 3.54 | | 2.05 |
| DC-2503 Cosmetic Wax[5] | 7.08 | 10.00 | 3.77 |
| Hydrophobic TiO2 | | | 0.50 |
| Iron oxide coated Mica | | | 0.65 |
| TiO2 Coated Mica | 1.00 | 1.00 | |
| Microcapsules of Example 1 | 0.8 | 0.8 | 0.8 |
| Microcapsules of Example 2 | 2.0 | 2.0 | 2.0 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate[6] | 0.10 | 0.10 | 0.10 |
| Niacinamide[7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | QS to 100 | QS to 100 | QS to 100 |
| Hardness at 21° C. (g) | 33.3 | 15.4 | 14.2 |
| Hardness at 33° C. (g) | 6.4 | 0.7 | 4.0 |

[1]12.5% Dimethicone Crosspolymer in Cyclopentasiloxane. Available from Dow Corning ™.
[2]E.g., Tospearl ™ 145A or Tospearl 2000. Available from GE Toshiba Silicone ™.
[3]25% Dimethicone PEG-10/15 Crosspolymer in Dimethicone. Available from Shin-Etsu ™.
[4]Jeenate ™ 3H polyethylene wax from Jeen ™
[5]Stearyl Dimethicone. Available from Dow Corning.
[6]Hexamidine disethionate, available from Laboratoires Serobiologiques.
[7]Additionally or alternatively, the composition may comprise one or more other skin care actives, their salts and derivatives, as disclosed herein, in amounts also disclosed herein as would be deemed suitable by one of skill in the art.

Example 22. Microcapsules in Single Unit Dose Personal Care Product

The following surfactant/polymer liquid processing composition is prepared at the indicated weight percentages as described in Table 1 below.

TABLE 1

| Component | |
| --- | --- |
| Glycerin | 3.2% |
| Polyvinyl alcohol[1] | 8.1% |
| Sodium Lauroamphoacetate (26% activity)[2] | 31.8% |
| Ammonium Laureth-3 sulfate (25% activity) | 4.9% |
| Ammonium Undecyl sulfate (24% activity) | 19.9% |
| Ammonium Laureth-1 sulfate (70% activity) | 8.0% |
| Cationic cellulose[3] | 0.5% |
| Citric Acid | 1.6% |
| Distilled water | 22.0% |
| Total | 100.0% |
| pH | 5.8 |
| Viscosity (cp) | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE ™ Polymer LR-400, available from Amerchol Corporation (Plaquemine, Louisiana)

A target weight of 300 grams of the above composition is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm. The cationic polymer, when present, is then slowly added with constant stirring until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between is 5.2-6.6 and adjusted with citric acid or diluted sodium hydroxide if necessary. The resulting processing mixture viscosity is measured.

A porous dissolvable solid substrate (also referred to in the examples herein as "substrate") is prepared from the above liquid processing mixture as described in Table 2 below.

TABLE 2

| Aeration Time (sec) | 62 |
| --- | --- |
| Wet Density (g/cm$^3$) | 0.26 |
| Oven Temperature (° C.) | 130 |
| Drying Time (min) | 38 |
| Average dry substrate weight (g) | 1.10 |
| Average dry substrate thickness (cm) | 0.62 |
| Average substrate shrinkage (%) | 4.6% |
| Average dry substrate density (g/cm$^3$) | 0.11 |
| Average basis weight (g/m$^2$) | 650 |

300 grams of the processing mixture is stored within a convection oven for greater than two hours at 70° C. to pre-heat the processing mixture. The mixture is then transferred into a pre-heated 5 quart stainless steel bowl (by placing into 70° C. oven for greater than 15 minutes) of a KITCHENAID® Mixer Model K5SS (available from Hobart Corporation, Troy, Ohio) fitted with a flat beater attachment and with a water bath attachment comprising tap water at 70-75° C. The mixture is vigorously aerated at a maximum speed setting of 10 until a wet density of approximately 0.26 grams/cm$^3$ is achieved (time recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45° angle and slowly dragged uniformly across the mold surface. The aluminum molds are then placed into a 130° C. convection oven for approximately 35 to 45 minutes. The molds are allowed to cool to room temperature with the substantially dry porous dissolvable solid substrates removed from the molds with the aid of a thin spatula and tweezers.

Each of the resulting 160 mm×160 mm square substrates is cut into nine 43 mm×43 mm squares (with rounded edges) using a cutting die and a Samco SB20 cutting machine (each square representing surface area of approximately 16.9 cm$^2$). The resulting smaller substrates are then equilibrated overnight (14 hours) in a constant environment room kept at 70° F. and 50% relative humidity within large zip-lock bags that are left open to the room atmosphere.

Within a fume hood, the substrate is mounted on a stainless steel easel that rests at about a 60 degree angle and with notches holding the substrate from sliding downward and with a hole in plate so that the substrate can easily be removed from the mount by pushing from the easel. It is important that the top surface of the substrate (the side that is exposed to the air in the drying oven and opposite the side that is in direct contact with the aluminum mold during the drying process) is facing away from the easel. A small glass bottle with a pump spray is filled with the primary perfume oil oil 1a and then sprayed onto the surface of the substrate from a distance of 2 to 3 inches. The substrate is then removed from the easel and returned to the weigh boat on the balance with the top side facing upwards. The weight of perfume applied is recorded and in the instance that the target weight is not achieved, either another spray amount is applied or a Kim wipe to absorb excess perfume away from the substrate. This iterative process is repeated until the target weight range is achieved. The amount of perfume oil 1a applied is recorded in the below table. The resulting substrate resting on the small weigh boat is stored within a zip-lock bag and sealed from the atmosphere. The above process is repeated on a second substrate.

The first substrate within its weigh boat is later removed from the zip-lock bag and tared again to zero weight on a 4 place weigh balance. A perfume microcapsule of Example 15 is then applied to the surface of each substrate. The substrate is coated with the perfume microcapsule powder by gently shaking the substrate in a tray (or other suitable container) containing an excess of the perfume microcapsules in a side-to-side manner ten times (the process is repeated for the other side). A perfume microcapsule of Example 16 is then applied to the surface of each substrate. A similar process is used to coat each side of the substrate as was done with perfume microcapsules of Example 15. The resulting powder coated substrate is then picked up (with gloved hands) and gently shaken and tapped several times to remove any excess powder that is not sufficiently adhered to the substrate. The resulting weight of the microcapsules of the secondary fragrances applied is recorded in the below table. The porous substrate within its weigh boat is then returned the zip lock bag and sealed from the atmosphere. This powder application process is repeated for the second substrate.

The final weights achieved are given in the below table:

| Substrate No. | Initial substrate weight | Weight of primary fragrance applied | Weight of perfume microcapsule powder (Example 15) | Weight of perfume microcapsules powder of Example 16 |
|---|---|---|---|---|
| 1 | 1.194 | 0.050 | 0.0175 | 0.0175 |
| 2 | 1.063 | 0.055 | 0.0150 | 0.0150 |
| Averages | 1.129 | 0.053 | 0.0161 | 0.0161 |

Fragrance capsules of example 15 and 16 in this example could be replaced by those of example 17, 18 or 19.

Examples 23A-23J. Microcapsules in Antiperspirant/Deodorant

| Ingredient | Ex. 23A | Ex. 23B | Ex. 23C | Ex. 23D | Ex. 23E |
|---|---|---|---|---|---|
| Part I: Partial Continuous Phase | | | | | |
| Hexamethyldisiloxane[1] | 22.65 | 21.25 | 21.25 | 21.25 | 21.25 |
| DC5200[2] | 1.20 | 1.20 | 1.20 | 1.20 | |
| Fragrance | 0.35 | 1.25 | 1.25 | 1.25 | 1.25 |
| Fragrance Capsules of Example 15 | 0.83 | 0.83 | 0.83 | 0.83 | 0.83 |
| Fragrance capsules of Example 16 | 2.15 | 2.15 | 2.15 | 2.15 | 2.15 |
| Shin Etsu KF 6038[3] | | | | | 1.20 |
| Part II: Disperse Phase | | | | | |
| ACH (40% solution)[4] | 40.00 | 55.0 | | | |
| IACH (34% solution)[5] | | 2.30 | 49.00 | | |
| ZAG (30% solution)[6] | | | | 52.30 | 52.30 |
| propylene glycol | 5.00 | | 5.00 | 5.00 | 5.00 |
| Water | 12.30 | | 3.30 | | |
| Part III: Structurant Plus Remainder of Continuous Phase | | | | | |
| FinSolve TN | 6.50 | 6.00 | 6.50 | 6.00 | 6.50 |
| Ozocrite Wax | | | | | 12.00 |
| Performalene PL[7] | 11.00 | 11.00 | 12.00 | 12.00 | |
| Aqueous Phase Conductivity (mS/cm) | 37.7 | 79.5 | 40.5 | 60.3 | 60.3 |

[1]DC 246 fluid from Dow Corning
[2]from Dow Corning
[3]from Shinetsu
[4]Standard aluminum chlorohydrate solution
[5]IACH solution stabilized with calcium
[6]IZAG solution stabilized with calcium
[7]from New Phase Technologies Fragrance capsules of example 15 and 16 in this example could be replaced by those of example 17, 18 or 19.

Examples 20A-20E can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

| | Example | | | | |
|---|---|---|---|---|---|
| | 23F | 23G | 23H | 23I | 23J |
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragrance | 0.5 | 0.5 | 0.5 | 0.5 | 0.5 |
| Microcapsules of Example 15 | 0.8 | 0.8 | 0.8 | 0.8 | 1.25 |
| Microcapsules of Example 16 | 2.1 | 2.1 | 2.1 | 2.1 | 1.63 |
| dihydromyrcenol | 0.3 | .1 | 0.3 | 0.5 | .1 |
| Linalool | 0.2 | .15 | 0.2 | 0.25 | .15 |
| Propellant (1,1 difluoroethane) | | | | | 40 |

QS - indicates that this material is used to bring the total to 100%.

Examples 20F to 20I can be made as follows: all ingredients except the fragrance, linalool, and dihydromyrcenol are combined in a suitable container and heated to about 85° C. to form a homogeneous liquid. The solution is then cooled to about 62° C. and then the fragrance, linalool, and dihydromyrcenol are added. The mixture is then poured into an appropriate container and allowed to solidify up cooling to ambient temperature.

Example 20J can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

Fragrance capsules of example 15 and 16 in this example could be replaced by those of example 17, 18 or 19.

Examples 24A-24F. Microcapsules in Rinse-Off Conditioner

| Examples | 24A | 24B | 24C | 24D | 24E | 24F |
|---|---|---|---|---|---|---|
| Premix | | | | | | |
| Aminosilicone-1 *1 | 0.50 | 0.50 | | | | |
| Aminosilicone-2 *2 | | | 0.50 | 0.50 | 0.50 | |
| PDMS | | | | | | 0.50 |
| Microcapsules of Example 1 | 0 | 0.8 | 0.8 | 0.8 | 0.8 | 0.8 |
| Microcapsules of Example 2 | 0 | 2.0 | 2.0 | 2.0 | 2.0 | 2.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

Definitions of Components
*1 Aminosilicone-1 (AMD): having an amine content of 0.12-0.15m mol/g and a viscosity of 3,000-8,000 mPa · s, which is water insoluble
*2 Aminosilicone-2 (TAS): having an amine content of 0.04-0.06m mol/g and a viscosity of 10,000-16,000 mPa · s, which is water insoluble Examples 25A and 25C. 21Fare prepared as follows:
Cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

Example 25B is prepared as follows:
Cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

Examples 26A-26C. Microcapsules in a Rinse-Off Formulation

| | Example | | |
|---|---|---|---|
| | 26A | 26B | 26C |
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |

-continued

|  | Example | | |
|---|---|---|---|
|  | 26A | 26B | 26C |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | Parts | Parts | Parts |
| Petrolatum (G2218 from Sonnerbonn) | 60 | 60 | 60 |
| Mineral Oil (Hydrobrite 1000 from Sonnerbonn) | 20 | 20 | 20 |
| Microcapsules of Example 1 | 5.7 | 5.7 | 5.7 |
| Microcapsules of Example 2 | 14.3 | 14.3 | 14.3 |
| III: Surfactant Phase:Benefit Phase Blending Ratio | 50:50 | 90:10 | 90:10 |

Example 27

The following is an example of a fine fragrance application. The microcapsules of EXAMPLES 1 & 2 may be included in Composition B as shown in below. Compositions A and B may be stored separately such as by storing in a dual-reservoir dispenser or in separate dispensers to prevent the destruction of the microcapsules in the presence of the ethanol.

| Composition A | (% w/w) |
|---|---|
| Ethanol (96%) | 74.88 |
| Fragrance | 14 |
| Water | 10.82 |
| Diethylamino Hydroxybenzol Hexyl Benzoate | 0.195 |
| Ethylhexyl Methoxycinnamate | 0.105 |

| Composition B | (% w/w) |
|---|---|
| Water | 92.5847 |
| Microcapsules of Example 1 | 3.0181 |
| Microcapsules of Example 2 | 3.0181 |
| Carbomer | 0.5018 |
| Phenoxyethanol | 0.2509 |
| Magnesium Chloride | 0.2456 |
| Sodium Hydroxide | 0.1254 |
| Disodium EDTA | 0.0836 |
| Polyvinyl alcohol | 0.0655 |
| Sodium Benzoate | 0.0409 |
| Potassium Sorbate | 0.0409 |
| Xanthan Gum | 0.0246 |

Example 28

Granular laundry detergent compositions for hand washing or washing machines, typically top-loading washing machines.

|  | 18A (wt %) | 18B (wt %) | 18C (wt %) | 18D (wt %) | 18E (wt %) | 18F (wt %) |
|---|---|---|---|---|---|---|
| Linear alkylbenzenesulfonate | 20 | 22 | 20 | 15 | 19.5 | 20 |
| $C_{12-14}$ Dimethylhydroxyethyl ammonium chloride | 0.7 | 0.2 | 1 | 0.6 | 0.0 | 0 |
| AE3S | 0.9 | 1 | 0.9 | 0.0 | 0.4 | 0.9 |
| AE7 | 0.0 | 0.0 | 0.0 | 1 | 0.1 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate ($SiO_2$:$Na_2O$ at ratio 1.6:1) | 7 | 5 | 2 | 3 | 3 | 5 |
| Sodium carbonate | 25 | 20 | 25 | 17 | 18 | 19 |
| Polyacrylate MW 4500 | 1 | 0.6 | 1 | 1 | 1.5 | 1 |
| Random graft copolymer[1] | 0.1 | 0.2 | 0.0 | 0.0 | 0.05 | 0.0 |
| Carboxymethyl cellulose | 1 | 0.3 | 1 | 1 | 1 | 1 |
| Stainzyme ® (20 mg active/g) | 0.1 | 0.2 | 0.1 | 0.2 | 0.1 | 0.1 |
| Protease (Savinase ®, 32.89 mg active/g) | 0.1 | 0.1 | 0.1 | 0.1 |  | 0.1 |
| Amylase-Natalase ® (8.65 mg active/g) | 0.1 | 0.0 | 0.1 | 0.0 | 0.1 | 0.1 |
| Lipase-Lipex ® (18 mg active/g) | 0.03 | 0.07 | 0.3 | 0.1 | 0.07 | 0.4 |

-continued

|  | 18A (wt %) | 18B (wt %) | 18C (wt %) | 18D (wt %) | 18E (wt %) | 18F (wt %) |
| --- | --- | --- | --- | --- | --- | --- |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| MgSO$_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet Dye (DV9 or DV99 or DV66) | 0.0 | 0.0 | 0.0003 | 0.0001 | 0.0001 | 0.0 |
| Neat Perfume [1] | 0.5 | 0.5 | 0.5 | 0.5 | 0.5 | 0.5 |
| Microcapsules [2] | 0.7 | 1.0 | 2.3 | 0.5 | 1.2 | 0.8 |
| Sulfate/Moisture | Balance | | | | | |

[1] Optional.
[2] Mixture of the microcapsules of Examples 15 & 16 at a 1:1 weight ratio or microcapsules of example 17, or example 18, or example 19

Example 29

Granular laundry detergent compositions typically for front-loading automatic washing machines.

|  | A (wt %) | B (wt %) | C (wt %) | D (wt %) | E (wt %) | F (wt %) |
| --- | --- | --- | --- | --- | --- | --- |
| Linear alkylbenzenesulfonate | 8 | 7.1 | 7 | 6.5 | 7.5 | 7.5 |
| AE3S | 0 | 4.8 | 1.0 | 5.2 | 4 | 4 |
| C12-14 Alkylsulfate | 1 | 0 | 1 | 0 | 0 | 0 |
| AE7 | 2.2 | 0 | 2.2 | 0 | 0 | 0 |
| C$_{10-12}$ Dimethyl hydroxyethylammonium chloride | 0.75 | 0.94 | 0.98 | 0.98 | 0 | 0 |
| Crystalline layered silicate (δ-Na$_2$Si$_2$O$_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R (SiO$_2$:Na$_2$O at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease-Purafect ® (84 mg active/g) | 0.2 | 0.2 | 0.3 | 0.15 | 0.12 | 0.13 |
| Amylase-Stainzyme Plus ® (20 mg active/g) | 0.2 | 0.15 | 0.2 | 0.3 | 0.15 | 0.15 |
| Lipase-Lipex ® (18.00 mg active/g) | 0.05 | 0.15 | 0.1 | 0 | 0 | 0 |
| Amylase-Natalase ® (8.65 mg active/g) | 0.1 | 0.2 | 0 | 0 | 0.15 | 0.15 |
| Cellulase-Celluclean ™ (15.6 mg active/g) | 0 | 0 | 0 | 0 | 0.1 | 0.1 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |
| MgSO$_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |
| Sulphonated zinc phthalocyanine (active) | 0.0007 | 0.0012 | 0.0007 | 0 | 0 | 0 |
| S-ACMC | 0.01 | 0.01 | 0 | 0.01 | 0 | 0 |
| Direct Violet 9 (active) | 0 | 0 | 0.0001 | 0.0001 | 0 | 0 |

-continued

|  | A (wt %) | B (wt %) | C (wt %) | D (wt %) | E (wt %) | F (wt %) |
|---|---|---|---|---|---|---|
| Neat Perfume [1] | 0.5 | 0.5 | 0.5 | 0.5 | 0.5 | 0.5 |
| Perfume Microcapsules [2] | 2.0 | 1.5 | 0.9 | 2.2 | 1.5 | 0.8 |
| Sulfate/Water & Miscellaneous | | | Balance | | | |

[1] Optional.
[2] Mixture of the microcapsules of Examples 15 & 16 at a 1:1 weight ratio.

The typical pH is about 10.

Example 30. Heavy Duty Liquid Laundry Detergent Compositions 15

|  | A (wt %) | B (wt %) | C (wt %) | D (wt %) | E (wt %) | F (wt %) | G (wt %) |
|---|---|---|---|---|---|---|---|
| AES $C_{12-15}$ alkyl ethoxy (1.8) sulfate | 11 | 10 | 4 | 6.32 | 0 | 0 | 0 |
| AE3S | 0 | 0 | 0 | 0 | 2.4 | 0 | 0 |
| Linear alkyl benzene sulfonate/sulfonic acid | 1.4 | 4 | 8 | 3.3 | 5 | 8 | 19 |
| HSAS | 3 | 5.1 | 3 | 0 | 0 | 0 | 0 |
| Sodium formate | 1.6 | 0.09 | 1.2 | 0.04 | 1.6 | 1.2 | 0.2 |
| Sodium hydroxide | 2.3 | 3.8 | 1.7 | 1.9 | 1.7 | 2.5 | 2.3 |
| Monoethanolamine | 1.4 | 1.49 | 1.0 | 0.7 | 0 | 0 | To pH 8.2 |
| Diethylene glycol | 5.5 | 0.0 | 4.1 | 0.0 | 0 | 0 | 0 |
| AE9 | 0.4 | 0.6 | 0.3 | 0.3 | 0 | 0 | 0 |
| AE8 | 0 | 0 | 0 | 0 | 0 | 0 | 20.0 |
| AE7 | 0 | 0 | 0 | 0 | 2.4 | 6 | 0 |
| Chelant (HEDP) | 0.15 | 0.15 | 0.11 | 0.07 | 0.5 | 0.11 | 0.8 |
| Citric Acid | 2.5 | 3.96 | 1.88 | 1.98 | 0.9 | 2.5 | 0.6 |
| $C_{12-14}$ dimethyl Amine Oxide | 0.3 | 0.73 | 0.23 | 0.37 | 0 | 0 | 0 |
| $C_{12-18}$ Fatty Acid | 0.8 | 1.9 | 0.6 | 0.99 | 1.2 | 0 | 15.0 |
| 4-formyl-phenylboronic acid | 0 | 0 | 0 | 0 | 0.05 | 0.02 | 0.01 |
| Borax | 1.43 | 1.5 | 1.1 | 0.75 | 0 | 1.07 | 0 |
| Ethanol | 1.54 | 1.77 | 1.15 | 0.89 | 0 | 3 | 7 |
| A compound having the following general structure: bis(($C_2H_5O$)($C_2H_4O$)$n$)($CH_3$)—$N^+$—$C_xH_{2x}$-$N^+$—($CH_3$)—bis(($C_2H_5O$)($C_2H_4O$)$n$), wherein $n$ = from 20 to 30, and $x$ = from 3 to 8, or sulphated or sulphonated variants thereof | 0.1 | 0 | 0 | 0 | 0 | 0 | 2.0 |
| Ethoxylated ($EO_{15}$) tetraethylene pentamine | 0.3 | 0.33 | 0.23 | 0.17 | 0.0 | 0.0 | 0 |
| Ethoxylated Polyethylenimine | 0 | 0 | 0 | 0 | 0 | 0 | 0.8 |
| Ethoxylated hexamethylene diamine | 0.8 | 0.81 | 0.6 | 0.4 | 1 | 1 | 0 |
| 1,2-Propanediol | 0.0 | 6.6 | 0.0 | 3.3 | 0.5 | 2 | 8.0 |
| Fluorescent Brightener | 0.2 | 0.1 | 0.05 | 0.3 | 0.15 | 0.3 | 0.2 |
| Hydrogenated castor oil derivative structurant | 0.1 | 0 | 0 | 0 | 0 | 0 | 0.1 |
| Perfume | 1.6 | 1.1 | 1.0 | 0.8 | 0.9 | 1.5 | 1.6 |
| Protease (40.6 mg active/g) | 0.8 | 0.6 | 0.7 | 0.9 | 0.7 | 0.6 | 1.5 |
| Mannanase: Mannaway ® (25 mg active/g) | 0.07 | 0.05 | 0.045 | 0.06 | 0.04 | 0.045 | 0.1 |
| Amylase: Stainzyme ® (15 mg active/g) | 0.3 | 0 | 0.3 | 0.1 | 0 | 0.4 | 0.1 |
| Amylase: Natalase ® (29 mg active/g) | 0 | 0.2 | 0.1 | 0.15 | 0.07 | 0 | 0.1 |
| Xyloglucanase (Whitezyme ®, 20 mg active/g) | 0.2 | 0.1 | 0 | 0 | 0.05 | 0.05 | 0.2 |
| Lipex ® (18 mg active/g) | 0.4 | 0.2 | 0.3 | 0.1 | 0.2 | 0 | 0 |
| Neat Perfume [1] | 0.5 | 0.5 | 0.5 | 0.5 | 0.5 | 0.5 | 0.5 |
| Perfume Microcapsules [2] | 0.25 | 3.2 | 2.5 | 4.0 | 2.5 | 1.4 | 0.8 |
| *Water, dyes & minors | | | | Balance | | | |

*Based on total cleaning and/or treatment composition weight, a total of no more than 12% water
[1] Optional.
[2] Mixture of the microcapsules of Examples 15 & 16 at a 1:1 weight ratio.

RAW MATERIALS AND NOTES FOR COMPOSITION EXAMPLES

LAS is linear alkylbenzenesulfonate having an average aliphatic carbon chain length $C_9$-$C_{15}$ supplied by Stepan, Northfield, Ill., USA or Huntsman Corp. (HLAS is acid form).

$C_{12-14}$ Dimethylhydroxyethyl ammonium chloride, supplied by Clariant GmbH, Germany AE3S is $C_{12-15}$ alkyl ethoxy (3) sulfate supplied by Stepan, Northfield, Ill., USA AE7 is $C_{12-15}$ alcohol ethoxylate, with an average degree of ethoxylation of 7, supplied by Huntsman, Salt Lake City, Utah, USA AES is $C_{10-18}$ alkyl ethoxy sulfate supplied by Shell Chemicals.

AE9 is $C_{12-13}$ alcohol ethoxylate, with an average degree of ethoxylation of 9, supplied by Huntsman, Salt Lake City, Utah, USA HSAS or HC1617HSAS is a mid-branched primary alkyl sulfate with average carbon chain length of about 16-17

Sodium tripolyphosphate is supplied by Rhodia, Paris, France

Zeolite A is supplied by Industrial Zeolite (UK) Ltd, Grays, Essex, UK 1.6R Silicate is supplied by Koma, Nestemica, Czech Republic Sodium Carbonate is supplied by Solvay, Houston, Tex., USA Polyacrylate MW 4500 is supplied by BASF, Ludwigshafen, Germany Carboxymethyl cellulose is Finnfix® V supplied by CP Kelco, Arnhem, Netherlands Suitable chelants are, for example, diethylenetetraamine pentaacetic acid (DTPA) supplied by Dow Chemical, Midland, Mich., USA or Hydroxyethane di phosphonate (HEDP) supplied by Solutia, St Louis, Mo., USA Bagsvaerd, Denmark Savinase®, Natalase®, Stainzyme®, Lipex®, Celluclean™, Mannaway® and Whitezyme® are all products of Novozymes, Bagsvaerd, Denmark.

Proteases may be supplied by Genencor International, Palo Alto, Calif., USA (e.g. Purafect Prime®) or by Novozymes, Bagsvaerd, Denmark (e.g. Liquanase®, Coronase®).

Fluorescent Brightener 1 is Tinopal® AMS, Fluorescent Brightener 2 is Tinopal® CBS-X, Sulphonated zinc phthalocyanine and Direct Violet 9 is Pergasol® Violet BN-Z all supplied by Ciba Specialty Chemicals, Basel, Switzerland Sodium percarbonate supplied by Solvay, Houston, Tex., USA Sodium perborate is supplied by Degussa, Hanau, Germany NOBS is sodium nonanoyloxybenzenesulfonate, supplied by Future Fuels, Batesville, USA TAED is tetraacetylethylenediamine, supplied under the Peractive® brand name by Clariant GmbH, Sulzbach, Germany S-ACMC is carboxymethylcellulose conjugated with C.I. Reactive Blue 19, sold by Megazyme, Wicklow, Ireland under the product name AZO-CM-CELLULOSE, product code S-ACMC.

Soil release agent is Repel-O-Tex® PF, supplied by Rhodia, Paris, France

Acrylic Acid/Maleic Acid Copolymer is molecular weight 70,000 and acrylate:maleate ratio 70:30, supplied by BASF, Ludwigshafen, Germany Na salt of Ethylenediamine-N,N'-disuccinic acid, (S,S) isomer (EDDS) is supplied by Octel, Ellesmere Port, UK Hydroxyethane di phosphonate (HEDP) is supplied by Dow Chemical, Midland, Mich., USA Suds suppressor agglomerate is supplied by Dow Corning, Midland, Mich., USA HSAS is mid-branched alkyl sulfate as disclosed in U.S. Pat. Nos. 6,020,303 and 6,060,443

$C_{12-14}$ dimethyl Amine Oxide is supplied by Procter & Gamble Chemicals, Cincinnati, USA Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40:60 and no more than 1 grafting point per 50 ethylene oxide units.

Ethoxylated polyethyleneimine is polyethyleneimine (MW=600) with 20 ethoxylate groups per —NH.

Cationic cellulose polymer is LK400, LR400 and/or JR30M from Amerchol Corporation, Edgewater N.J.

Note: all enzyme levels are expressed as % enzyme raw material.

Examples 31A-31E. Fabric Enhancer Solid Particle or Bead Composition

| Ingredients | Example 31A Active Wt % | Example 31B Active Wt % | Example 31C Active Wt % | Example 31D Active Wt % | Example 31E Active Wt % |
|---|---|---|---|---|---|
| PEG 8000 | 86.21 | 83.255 | 83.255 | 86.21 | 82.49 |
| Free (Neat) Perfume | 4.41 | 5.88 | 4.41 | 4.25 | 5.88 |
| Perfume Micro Capsule (PMC)[1] | 7.76 | 10.1 | 10.76 | 7.76 | 10.58 |
| Aesthetics Dye | 0.015 | 0.015 | 0.015 | 0.015 | 0.015 |

[1]Mixture of the microcapsules of Examples 15 & 16 at a 1:1 weight ratio.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a consumer product that provides multiple blooms of fragrance, the method comprising:
   combining a first adjunct material, a first population of microcapsules, and a second population of microcapsules to form the consumer product;
   wherein the first population has a first median volume weighted particle size and comprises microcapsules comprising a partitioning modifier and a first perfume oil at a first weight ratio; and
   wherein the second population of microcapsules has a second median volume weighted particle size and comprises microcapsules comprising the partitioning modifier and a second perfume oil at a second weight ratio;
   wherein the first median volume weighted particle size and the second median volume weighted particle size are different.

2. The method of claim 1, wherein at least one of the first population of microcapsules and the second population of microcapsules is contained in a slurry prior to combining with the adjunct material.

3. The method of claim 2, wherein the slurry includes one or more processing aids selected from the group consisting of a carrier, an aggregate inhibiting material, a deposition aid, a particle suspending polymer, and mixtures thereof.

4. The method of claim 1, wherein at least one of the first population of microcapsules and the second population of microcapsules is spray dried prior to combining with the adjunct material.

5. The method of claim 1, wherein the first weight ratio is a weight ratio of from 2:3 to 3:2 of the partitioning modifier to the first perfume oil; and wherein the second weight ratio is a weight ratio of greater than 0 to less than 2:3 of the partitioning modifier to the second perfume oil.

6. The method of claim 1, wherein a weight ratio of the first population of microcapsules to the second population of microcapsules is greater than 0 to less than 1:1.

7. The method of claim 1, wherein a weight ratio of the first population of microcapsules to the second population of microcapsules exceeds 1:1.

8. The method of claim 1, wherein the first and second median volume-weighted particle size is from 2 microns to 80 microns.

9. The method of claim 8, wherein the first and second median volume-weighted particle size is from 9 microns to 15 microns.

10. The method of claim 1, wherein the first population of microcapsules and the second population of microcapsules have a wall thickness of from 10 nm to 200 nm.

11. The method of claim 1, wherein the adjunct material comprises a non-encapsulated perfume oil.

12. The method of claim 11, wherein the non-encapsulated perfume oil is different from the first and second perfume oil.

13. The method of claim 1, wherein the partitioning modifier is selected from the group consisting of isopropyl myristate, mono-, di-, and tri-esters of $C_4$-$C_{24}$ fatty acids, castor oil, mineral oil, soybean oil, hexadecanoic acid, methyl ester isododecane, isoparaffin oil, polydimethylsiloxane, brominated vegetable oil, and mixtures thereof.

14. The method of claim 1, wherein the microcapsule further comprises a shell material selected from the group consisting of polyacrylates, polyethylenes, polyamides, polystyrenes, polyisoprenes, polycarbonates, polyesters, polyureas, polyurethanes, polyolefins, polysaccharides, epoxy resins, vinyl polymers, urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates; acrylate monomers polymerized via free radical polymerization, silk, wool, gelatine, cellulose, proteins, and mixtures thereof.

15. The method of claim 1, wherein the microcapsule further comprises a shell material comprising a reaction product of a first substance in the presence of a second substance comprising an emulsifier, the first substance comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator.

16. The method of claim 1, wherein the consumer product is a fabric and home care composition.

17. The method of claim 1, wherein the consumer product is a personal care composition.

18. The method of claim 1, wherein the consumer product further comprises a malodor reducing agent selected from the group consisting of pantothenic acid, petrolatum, menthyl acetate, uncomplexed cyclodextrin, talc, silica, and mixtures thereof.

19. The method of claim 1, wherein the first population of microcapsules and the second population of microcapsules have different partitioning modifiers.

20. The method of claim 1, wherein the adjunct material comprises a surfactant.

21. The method of claim 1, wherein the first perfume oil and the second perfume oil comprise at least one different material.

22. The method of claim 1, wherein the first population and second population comprise different shell materials.

23. The method of claim 1, wherein the first perfume oil and the second perfume oil are the same.

24. The method of claim 1, wherein at least one of the first population of microcapsules and the second population of microcapsules is contained in an agglomerate prior to combining with the adjunct material.

\* \* \* \* \*